(12) United States Patent
Filippov et al.

(10) Patent No.: US 8,114,639 B2
(45) Date of Patent: Feb. 14, 2012

(54) METHOD FOR PRODUCING AN L-AMINO ACID USING A BACTERIUM OF THE ENTEROBACTERIACEAE FAMILY WITH ATTENUATED EXPRESSION OF THE SFMACDFH-FIMZ CLUSTER OR THE FIMZ GENE

(75) Inventors: Dmitriy Vladimirovich Filippov, Moscow (RU); Vera Georgievna Doroshenko, Moscow (RU); Aleksandra Yurievna Skorokhodova, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 450 days.

(21) Appl. No.: 12/253,415

(22) Filed: Oct. 17, 2008

(65) Prior Publication Data

US 2009/0087886 A1 Apr. 2, 2009

Related U.S. Application Data

(63) Continuation of application No. PCT/JP2007/058902, filed on Apr. 18, 2007.

(60) Provisional application No. 60/829,923, filed on Oct. 18, 2006.

(30) Foreign Application Priority Data

Apr. 18, 2006 (RU) ................................ 2006112624

(51) Int. Cl.
*C12P 13/04* (2006.01)
(52) U.S. Cl. ........ 435/106; 435/107; 435/108; 435/109; 435/110; 435/113; 435/114; 435/115; 435/116; 435/252.3; 435/252.33
(58) Field of Classification Search .................. None
See application file for complete search history.

(56) References Cited

U.S. PATENT DOCUMENTS

| | | | |
|---|---|---|---|
| 5,175,107 A | 12/1992 | Debabov et al. | |
| 5,688,671 A | 11/1997 | Sugimoto et al. | |
| 5,932,453 A | 8/1999 | Kikuchi et al. | |
| 6,132,999 A | 10/2000 | Debabov et al. | |
| 6,303,348 B1 | 10/2001 | Livshits et al. | |
| 6,319,696 B1 | 11/2001 | Kishino et al. | |
| 6,960,455 B2 | 11/2005 | Livshits et al. | |
| 7,138,266 B2 | 11/2006 | Debabov et al. | |
| 7,179,623 B2 | 2/2007 | Livshits et al. | |
| 7,186,531 B2 | 3/2007 | Akhverdian et al. | |
| 7,259,003 B2 | 8/2007 | Livshits et al. | |
| 7,312,058 B2 | 12/2007 | Kashiwagi et al. | |
| 7,381,548 B2 | 6/2008 | Sheremet'eva et al. | |
| 7,422,880 B2 | 9/2008 | Rybak et al. | |
| 2002/0110878 A1 | 8/2002 | Moeckel et al. | |
| 2004/0132165 A1 | 7/2004 | Akhverdian et al. | |
| 2004/0229320 A1 | 11/2004 | Stoynova et al. | |
| 2005/0191684 A1* | 9/2005 | Zimenkov et al. | ........ 435/6 |
| 2005/0214911 A1 | 9/2005 | Marchenko et al. | |
| 2005/0239175 A1 | 10/2005 | Tabolina et al. | |
| 2005/0239177 A1 | 10/2005 | Livshits et al. | |
| 2006/0014257 A1 | 1/2006 | Katashkina et al. | |
| 2006/0035348 A1 | 2/2006 | Gulevich et al. | |
| 2006/0063240 A1 | 3/2006 | Katashkina et al. | |
| 2006/0088919 A1 | 4/2006 | Rybak et al. | |
| 2006/0216796 A1 | 9/2006 | Hashiguchi et al. | |
| 2007/0004014 A1 | 1/2007 | Tsuji et al. | |
| 2008/0113416 A1 | 5/2008 | Filippov et al. | |
| 2008/0153138 A1 | 6/2008 | Livshits et al. | |
| 2008/0261278 A1 | 10/2008 | Tabolina et al. | |
| 2008/0261279 A1 | 10/2008 | Tabolina et al. | |

FOREIGN PATENT DOCUMENTS

| | | |
|---|---|---|
| EP | 0 796 912 | 9/1997 |
| WO | WO02/22666 | 3/2002 |
| WO | WO03/054207 | 7/2003 |

OTHER PUBLICATIONS

Mori, H., English translation of Bioscience & Industry, vol. 562, p. 167, 2004, pp. 1-9.*
Hirakawa, H., et al., "β-Lactam resistance modulated by the overexpression of response regulators of two-component signal transduction systems in *Escherichia coil*," J. Antimicrobial Chemotherapy 2003;52:576-582.
International Preliminary Report on Patentability for PCT Patent App. No. PCT/JP2007/058902 (Oct. 30, 2008).
Blattner, F. R., et al., "The Complete Genome Sequence of *Escherichia coli* K-12," Science 1997;277:1453-1462.
Kaclíkova, E., et al., "Quantification of *Escherichia coli* by kinetic 5'-nuclease polymerase chain reaction (real-time PCR) oriented to *sfmD* gene," Lett. Appl Microbiol. 2005;41:132-135.
Riley, M., et al., "*Escherichia coil* K-12: a cooperatively developed annotation snapshot— 2005," Nucl. Acids Res. 2006;34(1):1-9.
Tinker, J. K., et al., "Characterization of FimY as a Coactivator of Type 1 Fimbrial Expression in *Salmonella enterica* Serovar Typhimurium," Infec. Immun. 2000;68(6):3305-3313.
Yeh, K-S., et al., "Construction and Characterization of a *fimZ* Mutant of *Salmonella typhimurium*," J. Bacteriol. 1995;177(23):6861-6865.
Yeh, K-S, et al., "FimZ Binds the *Salmonella typhimurium fimA* Promoter Region and May Regulate Its Own Expression with FimY," Microbiol. Immunol. 2002;46(1):1-10.
International Search Report and Written Opinion of the International Searching Authority for PCT Patent App. No. PCT/JP2007/058902 (Sep. 21, 2007).
U.S. Appl. No. 11/830,961, filed Jul. 31, 2007, Filippov et al.
U.S. Appl. No. 11/849,403, filed Sep. 4, 2007, Rybak et al.

(Continued)

*Primary Examiner* — Kade Ariani
(74) *Attorney, Agent, or Firm* — Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of the sfmACDFH-fimZ cluster and/or the fimZ gene.

7 Claims, 5 Drawing Sheets

OTHER PUBLICATIONS

U.S. Appl. No. 11/849,415, filed Sep. 4, 2007, Filippov et al.
U.S. Appl. No. 11/934,890, filed Nov. 5, 2007, Filippov et al.
U.S. Appl. No. 11/952,297, filed Dec. 7, 2007, Rybak et al.
U.S. Appl. No. 12/173,379, filed Jan. 22, 2008, Rybak et al.
U.S. Appl. No. 12/022,299, filed Jan. 30, 2008, Rybak et al.
U.S. Appl. No. 61/031,834, filed Feb. 27, 2008, Samsonov et al.
U.S. Appl. No. 61/046,081, filed Apr. 18, 2008, Gulevich et al.
U.S. Appl. No. 61/053,704, filed May 16, 2008, Rybak et al.
U.S. Appl. No. 12/125,988, filed May 23, 2008, Filippov et al.
U.S. Appl. No. 12/184,637, filed Aug. 1, 2008, Imaizumi et al.
U.S. Appl. No. 12/212,743, filed Sep. 18, 2008, Rybak et al.
U.S. Appl. No. 12/238,704, filed Sep. 26, 2008, Shakulov et al.

* cited by examiner

Obtained PCR product 1.7 kb)

SEQUENCE LISTING

```
<160> NUMBER OF SEQ ID NOS: 40

<210> SEQ ID NO 1
<211> LENGTH: 576
<212> TYPE: DNA
<213> ORGANISM: Escherichia coli
<220> FEATURE:
<221> NAME/KEY: CDS
<222> LOCATION: (1)..(576)

<400> SEQUENCE: 1 gtg gag tcg ata aat gag att gaa gga ata tat atg aaa tta aga ttt      48
Val Glu Ser Ile Asn Glu Ile Glu Gly Ile Tyr Met Lys Leu Arg Phe
1               5                  10                  15 att tcg tct gcg ctg gct gcc gca cta ttc gcc gct acg ggt agt tat      96
Ile Ser Ser Ala Leu Ala Ala Ala Leu Phe Ala Ala Thr Gly Ser Tyr
            20                  25                  30 gct gcc gtt gta gat ggc ggt aca att cac ttt gaa ggc gaa ctg gtg     144
Ala Ala Val Val Asp Gly Gly Thr Ile His Phe Glu Gly Glu Leu Val
        35                  40                  45 aat gct gcc tgt tca gtg aat act gac tcg gca gac cag gtt gtc aca     192
Asn Ala Ala Cys Ser Val Asn Thr Asp Ser Ala Asp Gln Val Val Thr
    50                  55                  60 ctc ggt caa tat cgt acc gat att ttc aat gct gtt ggt aat acc tct     240
Leu Gly Gln Tyr Arg Thr Asp Ile Phe Asn Ala Val Gly Asn Thr Ser
65                  70                  75                  80 gca tta att cca ttc acc att cag ttg aac gac tgc gat cct gtt gtt     288
Ala Leu Ile Pro Phe Thr Ile Gln Leu Asn Asp Cys Asp Pro Val Val
                85                  90                  95 gcc gct aat gct gcc gtt gca ttt tct ggt cag gct gat gca atc aat     336
Ala Ala Asn Ala Ala Val Ala Phe Ser Gly Gln Ala Asp Ala Ile Asn
            100                 105                 110 gat aat tta ttg gcc att gca tcc agt acc aat aca aca aca gca acg     384
Asp Asn Leu Leu Ala Ile Ala Ser Ser Thr Asn Thr Thr Thr Ala Thr
        115                 120                 125 ggt gtc ggt att gaa ata ctt gat aat aca tcc gca att ctc aaa cct     432
Gly Val Gly Ile Glu Ile Leu Asp Asn Thr Ser Ala Ile Leu Lys Pro
    130                 135                 140 gat ggg aat agc ttc tca acc aac cag aac ttg atc ccc ggg acc aac     480
Asp Gly Asn Ser Phe Ser Thr Asn Gln Asn Leu Ile Pro Gly Thr Asn
145                 150                 155                 160 gtt ctt cat ttt tct gca cgt tat aaa ggc acc ggt aca agt gca tca     528
Val Leu His Phe Ser Ala Arg Tyr Lys Gly Thr Gly Thr Ser Ala Ser
                165                 170                 175 gca ggg caa gca aat gct gac gcg act ttt att atg aga tat gaa taa     576
Ala Gly Gln Ala Asn Ala Asp Ala Thr Phe Ile Met Arg Tyr Glu
            180                 185                 190

<210> SEQ ID NO 2
<211> LENGTH: 191
<212> TYPE: PRT
```

<213> ORGANISM: Escherichia coli

<400> SEQUENCE: 2

```
Val Glu Ser Ile Asn Glu Ile Glu Gly Ile Tyr Met Lys Leu Arg Phe
1               5                   10                  15
Ile Ser Ser Ala Leu Ala Ala Ala Leu Phe Ala Ala Thr Gly Ser Tyr
            20                  25                  30
Ala Ala Val Val Asp Gly Gly Thr Ile His Phe Glu Gly Glu Leu Val
        35                  40                  45
Asn Ala Ala Cys Ser Val Asn Thr Asp Ser Ala Asp Gln Val Val Thr
    50                  55                  60
Leu Gly Gln Tyr Arg Thr Asp Ile Phe Asn Ala Val Gly Asn Thr Ser
65                  70                  75                  80
Ala Leu Ile Pro Phe Thr Ile Gln Leu Asn Asp Cys Asp Pro Val Val
                85                  90                  95
Ala Ala Asn Ala Ala Val Ala Phe Ser Gly Gln Ala Asp Ala Ile Asn
            100                 105                 110
Asp Asn Leu Leu Ala Ile Ala Ser Ser Thr Asn Thr Thr Ala Thr
        115                 120                 125
Gly Val Gly Ile Glu Ile Leu Asp Asn Thr Ser Ala Ile Leu Lys Pro
    130                 135                 140
Asp Gly Asn Ser Phe Ser Thr Asn Gln Asn Leu Ile Pro Gly Thr Asn
145                 150                 155                 160
Val Leu His Phe Ser Ala Arg Tyr Lys Gly Thr Gly Thr Ser Ala Ser
                165                 170                 175
Ala Gly Gln Ala Asn Ala Asp Ala Thr Phe Ile Met Arg Tyr Glu
            180                 185                 190
```

<210> SEQ ID NO 3
<211> LENGTH: 693
<212> TYPE: DNA
<213> ORGANISM: Escherichia coli
<220> FEATURE:
<221> NAME/KEY: CDS
<222> LOCATION: (1)..(693)

<400> SEQUENCE: 3

```
atg atg act aaa ata aag tta ttg atg ctc att ata ttt tat tta atc      48
Met Met Thr Lys Ile Lys Leu Leu Met Leu Ile Ile Phe Tyr Leu Ile
1               5                   10                  15 att tcg gcc agc gcc cat gct gcc gga ggg atc gca tta ggt gcc acg      96
Ile Ser Ala Ser Ala His Ala Ala Gly Gly Ile Ala Leu Gly Ala Thr
            20                  25                  30 cgt att att tat ccc gct gat gct aaa cag act gcg gta tgg att aga     144
Arg Ile Ile Tyr Pro Ala Asp Ala Lys Gln Thr Ala Val Trp Ile Arg
        35                  40                  45 aat agc cat acc aat gag cgc ttt ctg gtc aat tcg tgg att gaa aac     192
Asn Ser His Thr Asn Glu Arg Phe Leu Val Asn Ser Trp Ile Glu Asn
    50                  55                  60 agc agc ggt gta aaa gaa aag tca ttc atc att aca ccg cca ctg ttt     240
Ser Ser Gly Val Lys Glu Lys Ser Phe Ile Ile Thr Pro Pro Leu Phe
65                  70                  75                  80 gtt agt gaa ccc aaa agc gaa aat act ttg cgt att att tac acc ggt     288
Val Ser Glu Pro Lys Ser Glu Asn Thr Leu Arg Ile Ile Tyr Thr Gly
                85                  90                  95 cca ccg ctg gca gca gat cgt gag tct ctg ttc tgg atg aat gtt aag     336
Pro Pro Leu Ala Ala Asp Arg Glu Ser Leu Phe Trp Met Asn Val Lys
            100                 105                 110 acg atc cct tcg gta gat aaa aat gca ttg aac ggc agg aat gtt tg     384
```

```
                    Thr Ile Pro Ser Val Asp Lys Asn Ala Leu Asn Gly Arg Asn Val Leu
                            115                 120                 125 caa ctg gcg att tta tcg cgc atg aaa tta ttt ctc cgt cca att caa       432
Gln Leu Ala Ile Leu Ser Arg Met Lys Leu Phe Leu Arg Pro Ile Gln
    130                 135                 140 tta caa gaa tta ccc gca gaa gcg ccg gac aca ctc aag ttt tcg cga       480
Leu Gln Glu Leu Pro Ala Glu Ala Pro Asp Thr Leu Lys Phe Ser Arg
145                 150                 155                 160 tcc ggt aac tat atc aat gtt cat aat cca tca cct ttt tat gtc acc       528
Ser Gly Asn Tyr Ile Asn Val His Asn Pro Ser Pro Phe Tyr Val Thr
                165                 170                 175 ctg gtt aac tta caa gtg ggc agc caa aag ttg ggg aat gct atg gct       576
Leu Val Asn Leu Gln Val Gly Ser Gln Lys Leu Gly Asn Ala Met Ala
            180                 185                 190 gca ccc aga gtt aat tca caa att ccc tta ccc tca gga gtg cag gga       624
Ala Pro Arg Val Asn Ser Gln Ile Pro Leu Pro Ser Gly Val Gln Gly
        195                 200                 205 aag ctg aaa ttt cag acc gtt aat gat tat ggt tca gta act ccg gtc       672
Lys Leu Lys Phe Gln Thr Val Asn Asp Tyr Gly Ser Val Thr Pro Val
    210                 215                 220 aga gaa gtg aac tta aac taa                                           693
Arg Glu Val Asn Leu Asn
225                 230

<210> SEQ ID NO 4
<211> LENGTH: 230
<212> TYPE: PRT
<213> ORGANISM: Escherichia coli

<400> SEQUENCE: 4

Met Met Thr Lys Ile Lys Leu Leu Met Leu Ile Ile Phe Tyr Leu Ile
1               5                   10                  15

Ile Ser Ala Ser Ala His Ala Gly Gly Ile Ala Leu Gly Ala Thr
            20                  25                  30

Arg Ile Ile Tyr Pro Ala Asp Ala Lys Gln Thr Ala Val Trp Ile Arg
        35                  40                  45

Asn Ser His Thr Asn Glu Arg Phe Leu Val Asn Ser Trp Ile Glu Asn
    50                  55                  60

Ser Ser Gly Val Lys Glu Lys Ser Phe Ile Ile Thr Pro Pro Leu Phe
65                  70                  75                  80

Val Ser Glu Pro Lys Ser Glu Asn Thr Leu Arg Ile Ile Tyr Thr Gly
                85                  90                  95

Pro Pro Leu Ala Ala Asp Arg Glu Ser Leu Phe Trp Met Asn Val Lys
            100                 105                 110

Thr Ile Pro Ser Val Asp Lys Asn Ala Leu Asn Gly Arg Asn Val Leu
        115                 120                 125

Gln Leu Ala Ile Leu Ser Arg Met Lys Leu Phe Leu Arg Pro Ile Gln
    130                 135                 140

Leu Gln Glu Leu Pro Ala Glu Ala Pro Asp Thr Leu Lys Phe Ser Arg
145                 150                 155                 160

Ser Gly Asn Tyr Ile Asn Val His Asn Pro Ser Pro Phe Tyr Val Thr
                165                 170                 175

Leu Val Asn Leu Gln Val Gly Ser Gln Lys Leu Gly Asn Ala Met Ala
            180                 185                 190

Ala Pro Arg Val Asn Ser Gln Ile Pro Leu Pro Ser Gly Val Gln Gly
        195                 200                 205

Lys Leu Lys Phe Gln Thr Val Asn Asp Tyr Gly Ser Val Thr Pro Val
    210                 215                 220
```

Arg Glu Val Asn Leu Asn
225                 230

<210> SEQ ID NO 5
<211> LENGTH: 2604
<212> TYPE: DNA
<213> ORGANISM: Escherichia coli
<220> FEATURE:
<221> NAME/KEY: CDS
<222> LOCATION: (1)..(2604)

<400> SEQUENCE: 5

| | | | | | | | | | | | | | | | | |
|---|---|---|---|---|---|---|---|---|---|---|---|---|---|---|---|---|
| atg | aaa | ata | ccc | act | act | acg | gat | att | ccg | cag | agg | tat | acc | tgg | tgt | 48 |
| Met | Lys | Ile | Pro | Thr | Thr | Thr | Asp | Ile | Pro | Gln | Arg | Tyr | Thr | Trp | Cys | |
| 1 | | | | 5 | | | | | 10 | | | | | 15 | | |
| ctg | gcc | gga | att | tgt | tat | tca | tct | ctt | gcc | att | tta | ccc | tcc | ttt | tta | 96 |
| Leu | Ala | Gly | Ile | Cys | Tyr | Ser | Ser | Leu | Ala | Ile | Leu | Pro | Ser | Phe | Leu | |
| | | | | 20 | | | | | 25 | | | | | 30 | | |
| agc | tat | gcg | gaa | agt | tat | ttc | aac | ccg | gca | ttt | tta | tta | gag | aat | ggc | 144 |
| Ser | Tyr | Ala | Glu | Ser | Tyr | Phe | Asn | Pro | Ala | Phe | Leu | Leu | Glu | Asn | Gly | |
| | | | | 35 | | | | | 40 | | | | | 45 | | |
| aca | tcc | gtt | gct | gat | tta | tcg | cgc | ttt | gag | aga | ggt | aat | cat | caa | cct | 192 |
| Thr | Ser | Val | Ala | Asp | Leu | Ser | Arg | Phe | Glu | Arg | Gly | Asn | His | Gln | Pro | |
| | | 50 | | | | | 55 | | | | | 60 | | | | |
| gcg | ggc | gtg | tat | cgg | gtg | gat | ctc | tgg | cgt | aat | gat | gag | ttc | att | ggt | 240 |
| Ala | Gly | Val | Tyr | Arg | Val | Asp | Leu | Trp | Arg | Asn | Asp | Glu | Phe | Ile | Gly | |
| 65 | | | | | 70 | | | | | 75 | | | | | 80 | |
| tcg | cag | gat | atc | gta | ttt | gaa | tcg | aca | aca | gaa | aat | aca | ggt | gat | aaa | 288 |
| Ser | Gln | Asp | Ile | Val | Phe | Glu | Ser | Thr | Thr | Glu | Asn | Thr | Gly | Asp | Lys | |
| | | | | 85 | | | | | 90 | | | | | 95 | | |
| tca | ggt | ggg | tta | atg | ccc | tgt | ttt | aac | cag | gta | ctt | ctt | gaa | cga | att | 336 |
| Ser | Gly | Gly | Leu | Met | Pro | Cys | Phe | Asn | Gln | Val | Leu | Leu | Glu | Arg | Ile | |
| | | | | 100 | | | | | 105 | | | | | 110 | | |
| ggc | ctt | aat | agc | agt | gca | ttt | ccc | gag | tta | gcc | cag | cag | caa | aac | aat | 384 |
| Gly | Leu | Asn | Ser | Ser | Ala | Phe | Pro | Glu | Leu | Ala | Gln | Gln | Gln | Asn | Asn | |
| | | | | 115 | | | | | 120 | | | | | 125 | | |
| aaa | tgc | atc | aat | tta | ctg | aaa | gct | gta | cct | gat | gcc | aca | att | aac | ttt | 432 |
| Lys | Cys | Ile | Asn | Leu | Leu | Lys | Ala | Val | Pro | Asp | Ala | Thr | Ile | Asn | Phe | |
| | | 130 | | | | | 135 | | | | | 140 | | | | |
| gat | ttt | gca | gcg | atg | cgc | ctg | aac | atc | act | att | cct | cag | ata | gcg | ttg | 480 |
| Asp | Phe | Ala | Ala | Met | Arg | Leu | Asn | Ile | Thr | Ile | Pro | Gln | Ile | Ala | Leu | |
| 145 | | | | | 150 | | | | | 155 | | | | | 160 | |
| ttg | agc | agc | gct | cac | ggt | tac | att | ccg | cct | gaa | gag | tgg | gat | gaa | ggt | 528 |
| Leu | Ser | Ser | Ala | His | Gly | Tyr | Ile | Pro | Pro | Glu | Glu | Trp | Asp | Glu | Gly | |
| | | | | 165 | | | | | 170 | | | | | 175 | | |
| att | cct | gct | tta | ctc | ctg | aat | tat | aat | ttc | acc | ggt | aac | aga | ggt | aat | 576 |
| Ile | Pro | Ala | Leu | Leu | Leu | Asn | Tyr | Asn | Phe | Thr | Gly | Asn | Arg | Gly | Asn | |
| | | | | 180 | | | | | 185 | | | | | 190 | | |
| ggt | aac | gat | agc | tat | ttt | ttt | agt | gag | ctc | agc | ggg | att | aat | att | ggc | 624 |
| Gly | Asn | Asp | Ser | Tyr | Phe | Phe | Ser | Glu | Leu | Ser | Gly | Ile | Asn | Ile | Gly | |
| | | 195 | | | | | 200 | | | | | 205 | | | | |
| ccg | tgg | cgt | tta | cgc | aac | aat | ggt | tcc | tgg | aac | tat | ttt | cgc | gga | aat | 672 |
| Pro | Trp | Arg | Leu | Arg | Asn | Asn | Gly | Ser | Trp | Asn | Tyr | Phe | Arg | Gly | Asn | |
| 210 | | | | | 215 | | | | | 220 | | | | | | |
| gga | tat | cat | tca | gaa | cag | tgg | aat | aat | att | ggc | acc | tgg | gta | cag | cgc | 720 |
| Gly | Tyr | His | Ser | Glu | Gln | Trp | Asn | Asn | Ile | Gly | Thr | Trp | Val | Gln | Arg | |
| 225 | | | | | 230 | | | | | 235 | | | | | 240 | |
| gcc | att | att | ccg | ctg | aaa | agt | gaa | ctg | gta | atg | gga | gac | ggc | aat | aca | 768 |
| Ala | Ile | Ile | Pro | Leu | Lys | Ser | Glu | Leu | Val | Met | Gly | Asp | Gly | Asn | Thr | |
| | | | | 245 | | | | | 250 | | | | | 255 | | |
| gga | agt | gat | att | ttc | gat | ggc | gtt | gga | ttt | cgt | ggt | gta | cgg | ctt | tat | 816 |

```
                                                        -continued

Gly Ser Asp Ile Phe Asp Gly Val Gly Phe Arg Gly Val Arg Leu Tyr
            260                 265                 270 tct tct gat aat atg tat cct gat agc cag caa ggg ttt gcc cca acg      864
Ser Ser Asp Asn Met Tyr Pro Asp Ser Gln Gln Gly Phe Ala Pro Thr
            275                 280                 285 gta cgt ggg att gcc cgt acg gcg gcc cag cta acg att cgg caa aat      912
Val Arg Gly Ile Ala Arg Thr Ala Ala Gln Leu Thr Ile Arg Gln Asn
            290                 295                 300 ggt ttt att atc tat caa agc tat gtt tcc ccc ggc gct ttt gaa att      960
Gly Phe Ile Ile Tyr Gln Ser Tyr Val Ser Pro Gly Ala Phe Glu Ile
305                 310                 315                 320 aca gat ttg cac ccg aca tct tca aat ggc gat ctg gac gtc acc atc     1008
Thr Asp Leu His Pro Thr Ser Ser Asn Gly Asp Leu Asp Val Thr Ile
                325                 330                 335 gac gag cgc gat ggc aat cag cag aat tac aca att ccg tat tca aca     1056
Asp Glu Arg Asp Gly Asn Gln Gln Asn Tyr Thr Ile Pro Tyr Ser Thr
            340                 345                 350 gtg cca att tta caa cgc gaa ggg cgt ttc aaa ttt gac ctg acg gcg     1104
Val Pro Ile Leu Gln Arg Glu Gly Arg Phe Lys Phe Asp Leu Thr Ala
            355                 360                 365 ggc gat ttt cgt agc ggt aat agt cag caa tca tcg cct ttc ttt ttt     1152
Gly Asp Phe Arg Ser Gly Asn Ser Gln Gln Ser Ser Pro Phe Phe Phe
370                 375                 380 cag ggt acg gca ctc ggc ggt tta cca cag gaa ttt act gcc tac ggc     1200
Gln Gly Thr Ala Leu Gly Gly Leu Pro Gln Glu Phe Thr Ala Tyr Gly
385                 390                 395                 400 ggg acg caa tta tct gcc aat tac acc gcc ttt tta tta ggg ctg ggg     1248
Gly Thr Gln Leu Ser Ala Asn Tyr Thr Ala Phe Leu Leu Gly Leu Gly
                405                 410                 415 cgc aat ctc ggg aac tgg ggc gca gtg tcg ctg gat gta acg cat gcg     1296
Arg Asn Leu Gly Asn Trp Gly Ala Val Ser Leu Asp Val Thr His Ala
            420                 425                 430 cgc agt cag tta gcc gac gcc agt cgt cat gag ggg gat tct att cgc     1344
Arg Ser Gln Leu Ala Asp Ala Ser Arg His Glu Gly Asp Ser Ile Arg
            435                 440                 445 ttc ctc tat gcg aaa tcg atg aac acc ttc ggc acc aat ttt cag tta     1392
Phe Leu Tyr Ala Lys Ser Met Asn Thr Phe Gly Thr Asn Phe Gln Leu
            450                 455                 460 atg ggt tac cgc tat tcg aca caa ggt ttt tat acc ctt gat gat gtt     1440
Met Gly Tyr Arg Tyr Ser Thr Gln Gly Phe Tyr Thr Leu Asp Asp Val
465                 470                 475                 480 gcg tat cgt cga atg gag ggg tac gaa tat gat tac gac ggt gag cat     1488
Ala Tyr Arg Arg Met Glu Gly Tyr Glu Tyr Asp Tyr Asp Gly Glu His
                485                 490                 495 cgc gat gaa ccg ata atc gtg aat tac cac aat tta cgc ttt agc cgt     1536
Arg Asp Glu Pro Ile Ile Val Asn Tyr His Asn Leu Arg Phe Ser Arg
            500                 505                 510 aaa gac cgt ttg cag tta aat gtt tca caa tca ctt aat gac ttt ggc     1584
Lys Asp Arg Leu Gln Leu Asn Val Ser Gln Ser Leu Asn Asp Phe Gly
            515                 520                 525 tcg ctt tat att tct ggt acc cat caa aaa tac tgg aat act tcg gat     1632
Ser Leu Tyr Ile Ser Gly Thr His Gln Lys Tyr Trp Asn Thr Ser Asp
530                 535                 540 tca gat acg tgg tat cag gtg ggg tat acc agc agc tgg gtt ggc atc     1680
Ser Asp Thr Trp Tyr Gln Val Gly Tyr Thr Ser Ser Trp Val Gly Ile
545                 550                 555                 560 agt tat tcg ctc tca ttt tcg tgg aat gaa tct gta ggg atc ccc gat     1728
Ser Tyr Ser Leu Ser Phe Ser Trp Asn Glu Ser Val Gly Ile Pro Asp
                565                 570                 575 aac gaa cgt att gtc gga ctt aat gtt tca gtg cct ttc aat gtt ttg     1776
```

|  |  |  |  |  |  |  |  |  |  |  |  |  |
|---|---|---|---|---|---|---|---|---|---|---|---|---|
| Asn | Glu | Arg | Ile | Val | Gly | Leu | Asn | Val | Ser | Val | Pro | Phe | Asn | Val | Leu |
|  |  |  | 580 |  |  |  | 585 |  |  |  | 590 |  |  |  |  |

```
acc aaa cgt cgc tac acc cgg gaa aat gcg ctc gac cgc gct tat gcc   1824
Thr Lys Arg Arg Tyr Thr Arg Glu Asn Ala Leu Asp Arg Ala Tyr Ala
        595                 600                 605 tcc ttt aac gcc aac cgt aac agc aac ggg caa aat agc tgg ctg gca   1872
Ser Phe Asn Ala Asn Arg Asn Ser Asn Gly Gln Asn Ser Trp Leu Ala
    610                 615                 620 ggt gta ggt ggg acc tta ctg gaa ggc cac aac ctg agt tat cac gta   1920
Gly Val Gly Gly Thr Leu Leu Glu Gly His Asn Leu Ser Tyr His Val
625                 630                 635                 640 agc cag ggt gat acc tcg aat aat ggg tac acg ggc agc gcc acg gca   1968
Ser Gln Gly Asp Thr Ser Asn Asn Gly Tyr Thr Gly Ser Ala Thr Ala
                645                 650                 655 aac tgg cag gcc gct tac ggt acg ctg ggg ggc ggg tat aac tac gac   2016
Asn Trp Gln Ala Ala Tyr Gly Thr Leu Gly Gly Gly Tyr Asn Tyr Asp
            660                 665                 670 cgc gat caa cat gac gtt aac tgg cag ctg tct ggc ggt gtg gtc ggg   2064
Arg Asp Gln His Asp Val Asn Trp Gln Leu Ser Gly Gly Val Val Gly
        675                 680                 685 cat gaa aat ggc ata acg ctg agc cag cct tta ggg gat acc aat gtt   2112
His Glu Asn Gly Ile Thr Leu Ser Gln Pro Leu Gly Asp Thr Asn Val
    690                 695                 700 ttg att aaa gcg cct ggc gca ggc ggt gta cgc att gaa aat caa act   2160
Leu Ile Lys Ala Pro Gly Ala Gly Gly Val Arg Ile Glu Asn Gln Thr
705                 710                 715                 720 ggc att tta acc gac tgg cgc ggc tat gcg gtg atg ctg tat gcc acg   2208
Gly Ile Leu Thr Asp Trp Arg Gly Tyr Ala Val Met Leu Tyr Ala Thr
                725                 730                 735 gtt tat cgg tat aac cgt atc gcg ctt gat acc aat acg atg ggg aat   2256
Val Tyr Arg Tyr Asn Arg Ile Ala Leu Asp Thr Asn Thr Met Gly Asn
            740                 745                 750 tcc atc gat gtt gaa aaa aat att agc agc gtt gtg ccg acg caa ggc   2304
Ser Ile Asp Val Glu Lys Asn Ile Ser Ser Val Val Pro Thr Gln Gly
        755                 760                 765 gcg ttg gtt cgt gcc aat ttt gat acc cgc ata ggc gtg cgg gcg ctc   2352
Ala Leu Val Arg Ala Asn Phe Asp Thr Arg Ile Gly Val Arg Ala Leu
    770                 775                 780 att acc gtt acc cag ggc gga aaa ccg gtg ccg ttt gga tca ctg gta   2400
Ile Thr Val Thr Gln Gly Gly Lys Pro Val Pro Phe Gly Ser Leu Val
785                 790                 795                 800 cgg gaa aac agt acc gga ata acc agt atg gtg ggt gat gac ggg caa   2448
Arg Glu Asn Ser Thr Gly Ile Thr Ser Met Val Gly Asp Asp Gly Gln
                805                 810                 815 gtt tat tta agt ggt gcg cca ttg tct ggt gaa tta ctg gtt cag tgg   2496
Val Tyr Leu Ser Gly Ala Pro Leu Ser Gly Glu Leu Leu Val Gln Trp
            820                 825                 830 gga gac ggc gcg aac tca cgc tgc att gcg cac tat gta ttg ccg aag   2544
Gly Asp Gly Ala Asn Ser Arg Cys Ile Ala His Tyr Val Leu Pro Lys
        835                 840                 845 caa agc tta cag caa gcc gtc act gtt att tcg gca gtt tgc aca cat   2592
Gln Ser Leu Gln Gln Ala Val Thr Val Ile Ser Ala Val Cys Thr His
    850                 855                 860 cct ggc tca taa                                                    2604
Pro Gly Ser
865

<210> SEQ ID NO 6
<211> LENGTH: 867
<212> TYPE: PRT
<213> ORGANISM: Escherichia coli
```

<400> SEQUENCE: 6

```
Met Lys Ile Pro Thr Thr Thr Asp Ile Pro Gln Arg Tyr Thr Trp Cys
1               5                   10                  15

Leu Ala Gly Ile Cys Tyr Ser Ser Leu Ala Ile Leu Pro Ser Phe Leu
            20                  25                  30

Ser Tyr Ala Glu Ser Tyr Phe Asn Pro Ala Phe Leu Leu Glu Asn Gly
        35                  40                  45

Thr Ser Val Ala Asp Leu Ser Arg Phe Glu Arg Gly Asn His Gln Pro
    50                  55                  60

Ala Gly Val Tyr Arg Val Asp Leu Trp Arg Asn Asp Glu Phe Ile Gly
65                  70                  75                  80

Ser Gln Asp Ile Val Phe Glu Ser Thr Thr Glu Asn Thr Gly Asp Lys
            85                  90                  95

Ser Gly Gly Leu Met Pro Cys Phe Asn Gln Val Leu Leu Glu Arg Ile
        100                 105                 110

Gly Leu Asn Ser Ser Ala Phe Pro Glu Leu Ala Gln Gln Asn Asn
    115                 120                 125

Lys Cys Ile Asn Leu Leu Lys Ala Val Pro Asp Ala Thr Ile Asn Phe
130                 135                 140

Asp Phe Ala Ala Met Arg Leu Asn Ile Thr Ile Pro Gln Ile Ala Leu
145                 150                 155                 160

Leu Ser Ser Ala His Gly Tyr Ile Pro Pro Glu Glu Trp Asp Glu Gly
            165                 170                 175

Ile Pro Ala Leu Leu Leu Asn Tyr Asn Phe Thr Gly Asn Arg Gly Asn
        180                 185                 190

Gly Asn Asp Ser Tyr Phe Phe Ser Glu Leu Ser Gly Ile Asn Ile Gly
    195                 200                 205

Pro Trp Arg Leu Arg Asn Asn Gly Ser Trp Asn Tyr Phe Arg Gly Asn
210                 215                 220

Gly Tyr His Ser Glu Gln Trp Asn Asn Ile Gly Thr Trp Val Gln Arg
225                 230                 235                 240

Ala Ile Ile Pro Leu Lys Ser Glu Leu Val Met Gly Asp Gly Asn Thr
            245                 250                 255

Gly Ser Asp Ile Phe Asp Gly Val Gly Phe Arg Gly Val Arg Leu Tyr
        260                 265                 270

Ser Ser Asp Asn Met Tyr Pro Asp Ser Gln Gln Gly Phe Ala Pro Thr
    275                 280                 285

Val Arg Gly Ile Ala Arg Thr Ala Ala Gln Leu Thr Ile Arg Gln Asn
290                 295                 300

Gly Phe Ile Ile Tyr Gln Ser Tyr Val Ser Pro Gly Ala Phe Glu Ile
305                 310                 315                 320

Thr Asp Leu His Pro Thr Ser Ser Asn Gly Asp Leu Asp Val Thr Ile
            325                 330                 335

Asp Glu Arg Asp Gly Asn Gln Gln Asn Tyr Thr Ile Pro Tyr Ser Thr
        340                 345                 350

Val Pro Ile Leu Gln Arg Glu Gly Arg Phe Lys Phe Asp Leu Thr Ala
    355                 360                 365

Gly Asp Phe Arg Ser Gly Asn Ser Gln Ser Ser Pro Phe Phe Phe
370                 375                 380

Gln Gly Thr Ala Leu Gly Gly Leu Pro Gln Glu Phe Thr Ala Tyr Gly
385                 390                 395                 400

Gly Thr Gln Leu Ser Ala Asn Tyr Thr Ala Phe Leu Leu Gly Leu Gly
            405                 410                 415
```

Arg Asn Leu Gly Asn Trp Gly Ala Val Ser Leu Asp Val Thr His Ala
            420                 425                 430

Arg Ser Gln Leu Ala Asp Ala Ser Arg His Glu Gly Asp Ser Ile Arg
            435                 440                 445

Phe Leu Tyr Ala Lys Ser Met Asn Thr Phe Gly Thr Asn Phe Gln Leu
450                 455                 460

Met Gly Tyr Arg Tyr Ser Thr Gln Gly Phe Tyr Thr Leu Asp Asp Val
465                 470                 475                 480

Ala Tyr Arg Arg Met Glu Gly Tyr Glu Tyr Asp Tyr Asp Gly Glu His
            485                 490                 495

Arg Asp Glu Pro Ile Ile Val Asn Tyr His Asn Leu Arg Phe Ser Arg
            500                 505                 510

Lys Asp Arg Leu Gln Leu Asn Val Ser Gln Ser Leu Asn Asp Phe Gly
            515                 520                 525

Ser Leu Tyr Ile Ser Gly Thr His Gln Lys Tyr Trp Asn Thr Ser Asp
            530                 535                 540

Ser Asp Thr Trp Tyr Gln Val Gly Tyr Thr Ser Ser Trp Val Gly Ile
545                 550                 555                 560

Ser Tyr Ser Leu Ser Phe Ser Trp Asn Glu Ser Val Gly Ile Pro Asp
            565                 570                 575

Asn Glu Arg Ile Val Gly Leu Asn Val Ser Val Pro Phe Asn Val Leu
            580                 585                 590

Thr Lys Arg Arg Tyr Thr Arg Glu Asn Ala Leu Asp Arg Ala Tyr Ala
            595                 600                 605

Ser Phe Asn Ala Asn Arg Asn Ser Asn Gly Gln Asn Ser Trp Leu Ala
610                 615                 620

Gly Val Gly Gly Thr Leu Leu Glu Gly His Asn Leu Ser Tyr His Val
625                 630                 635                 640

Ser Gln Gly Asp Thr Ser Asn Asn Gly Tyr Thr Gly Ser Ala Thr Ala
            645                 650                 655

Asn Trp Gln Ala Ala Tyr Gly Thr Leu Gly Gly Gly Tyr Asn Tyr Asp
            660                 665                 670

Arg Asp Gln His Asp Val Asn Trp Gln Leu Ser Gly Gly Val Val Gly
            675                 680                 685

His Glu Asn Gly Ile Thr Leu Ser Gln Pro Leu Gly Asp Thr Asn Val
            690                 695                 700

Leu Ile Lys Ala Pro Gly Ala Gly Gly Val Arg Ile Glu Asn Gln Thr
705                 710                 715                 720

Gly Ile Leu Thr Asp Trp Arg Gly Tyr Ala Val Met Leu Tyr Ala Thr
            725                 730                 735

Val Tyr Arg Tyr Asn Arg Ile Ala Leu Asp Thr Asn Thr Met Gly Asn
            740                 745                 750

Ser Ile Asp Val Glu Lys Asn Ile Ser Ser Val Pro Thr Gln Gly
            755                 760                 765

Ala Leu Val Arg Ala Asn Phe Asp Thr Arg Ile Gly Val Arg Ala Leu
            770                 775                 780

Ile Thr Val Thr Gln Gly Gly Lys Pro Val Pro Phe Gly Ser Leu Val
785                 790                 795                 800

Arg Glu Asn Ser Thr Gly Ile Thr Ser Met Val Gly Asp Asp Gly Gln
            805                 810                 815

Val Tyr Leu Ser Gly Ala Pro Leu Ser Gly Glu Leu Leu Val Gln Trp
            820                 825                 830

Gly Asp Gly Ala Asn Ser Arg Cys Ile Ala His Tyr Val Leu Pro Lys

```
                    835                 840                 845
      Gln Ser Leu Gln Gln Ala Val Thr Val Ile Ser Ala Val Cys Thr His
              850                 855                 860

Pro Gly Ser
      865

<210> SEQ ID NO 7
<211> LENGTH: 978
<212> TYPE: DNA
<213> ORGANISM: Escherichia coli
<220> FEATURE:
<221> NAME/KEY: CDS
<222> LOCATION: (1)..(978)

<400> SEQUENCE: 7 atg gca tgt ttg tgt ctg gca aac ata tcc tgg gct act gtt tgt gca      48
Met Ala Cys Leu Cys Leu Ala Asn Ile Ser Trp Ala Thr Val Cys Ala
1               5                   10                  15 aat agt act ggc gta gca gaa gat gaa cac tat gat ctc tca aat atc      96
Asn Ser Thr Gly Val Ala Glu Asp Glu His Tyr Asp Leu Ser Asn Ile
                20                  25                  30 ttt aat agc acc aat aac cag cca ggg cag att gtt gtt tta ccg gaa     144
Phe Asn Ser Thr Asn Asn Gln Pro Gly Gln Ile Val Val Leu Pro Glu
            35                  40                  45 aaa tcc ggc tgg gta ggt gtc tca gca att tgt cca ccc ggt acg ctg     192
Lys Ser Gly Trp Val Gly Val Ser Ala Ile Cys Pro Pro Gly Thr Leu
    50                  55                  60 gtg aat tat aca tac cgt agt tat gtc acc aac ttt att gtt cag gaa     240
Val Asn Tyr Thr Tyr Arg Ser Tyr Val Thr Asn Phe Ile Val Gln Glu
65                  70                  75                  80 act atc gat aat tat aaa tat atg caa tta cat gat tat cta tta ggt     288
Thr Ile Asp Asn Tyr Lys Tyr Met Gln Leu His Asp Tyr Leu Leu Gly
                85                  90                  95 gcg atg agt ctg gtt gat agt gtg atg gat att cag ttc ccc ccg caa     336
Ala Met Ser Leu Val Asp Ser Val Met Asp Ile Gln Phe Pro Pro Gln
            100                 105                 110 aat tat att cgg atg gga aca gat cct aac gtt tcg caa aac ctt cca     384
Asn Tyr Ile Arg Met Gly Thr Asp Pro Asn Val Ser Gln Asn Leu Pro
        115                 120                 125 ttc ggg gtg atg gat tct cgt tta ata ttt cgt tta aag gtt att cgt     432
Phe Gly Val Met Asp Ser Arg Leu Ile Phe Arg Leu Lys Val Ile Arg
    130                 135                 140 ccc ttt att aac atg gtg gag atc ccc aga cag gtg atg ttt acc gtg     480
Pro Phe Ile Asn Met Val Glu Ile Pro Arg Gln Val Met Phe Thr Val
145                 150                 155                 160 tat gtg aca tca acg cct tac gat ccg ttg gtt aca cct gtt tat acc     528
Tyr Val Thr Ser Thr Pro Tyr Asp Pro Leu Val Thr Pro Val Tyr Thr
                165                 170                 175 att agt ttt ggt ggc cgg gtt gaa gta ccg caa aac tgc gaa tta aat     576
Ile Ser Phe Gly Gly Arg Val Glu Val Pro Gln Asn Cys Glu Leu Asn
            180                 185                 190 gcc ggg cag att gtt gaa ttt gat ttt ggt gat atc ggc gca tcg tta     624
Ala Gly Gln Ile Val Glu Phe Asp Phe Gly Asp Ile Gly Ala Ser Leu
        195                 200                 205 ttt agt gcg gca ggg ccg ggt aat cga cct gct ggt gtc atg ccg caa     672
Phe Ser Ala Ala Gly Pro Gly Asn Arg Pro Ala Gly Val Met Pro Gln
    210                 215                 220 acc aag agc att gcg gtc aaa tgt acg aat gtt gct gcg cag gct tat     720
Thr Lys Ser Ile Ala Val Lys Cys Thr Asn Val Ala Ala Gln Ala Tyr
225                 230                 235                 240 tta aca atg cgt ctg gaa gcc agt gcc gtt tct ggt cag gcg atg gtg     768
Leu Thr Met Arg Leu Glu Ala Ser Ala Val Ser Gly Gln Ala Met Val
```

```
Leu Thr Met Arg Leu Glu Ala Ser Ala Val Ser Gly Gln Ala Met Val
            245                 250                 255 tcg gac aat cag gat tta ggt ttt att gtc gcc gat cag aac gat acg     816
Ser Asp Asn Gln Asp Leu Gly Phe Ile Val Ala Asp Gln Asn Asp Thr
            260                 265                 270 ccg atc acg cct aac gat ctc aat agc gtt att cct ttc cgt ctg gat     864
Pro Ile Thr Pro Asn Asp Leu Asn Ser Val Ile Pro Phe Arg Leu Asp
            275                 280                 285 gca gct gcg gca gcc aat gtc aca ctt cgc gcc tgg cct atc agt att     912
Ala Ala Ala Ala Ala Asn Val Thr Leu Arg Ala Trp Pro Ile Ser Ile
        290                 295                 300 acc ggt caa aaa ccg acc gaa ggg ccg ttt agc gcg ctg ggg tat tta     960
Thr Gly Gln Lys Pro Thr Glu Gly Pro Phe Ser Ala Leu Gly Tyr Leu
305                 310                 315                 320 cgc gtc gat tat caa tga                                             978
Arg Val Asp Tyr Gln
            325

<210> SEQ ID NO 8
<211> LENGTH: 325
<212> TYPE: PRT
<213> ORGANISM: Escherichia coli

<400> SEQUENCE: 8

Met Ala Cys Leu Cys Leu Ala Asn Ile Ser Trp Ala Thr Val Cys Ala
1               5                   10                  15

Asn Ser Thr Gly Val Ala Glu Asp Glu His Tyr Asp Leu Ser Asn Ile
            20                  25                  30

Phe Asn Ser Thr Asn Asn Gln Pro Gly Gln Ile Val Val Leu Pro Glu
        35                  40                  45

Lys Ser Gly Trp Val Gly Val Ser Ala Ile Cys Pro Pro Gly Thr Leu
50                  55                  60

Val Asn Tyr Thr Tyr Arg Ser Tyr Val Thr Asn Phe Ile Val Gln Glu
65                  70                  75                  80

Thr Ile Asp Asn Tyr Lys Tyr Met Gln Leu His Asp Tyr Leu Leu Gly
            85                  90                  95

Ala Met Ser Leu Val Asp Ser Val Met Asp Ile Gln Phe Pro Pro Gln
            100                 105                 110

Asn Tyr Ile Arg Met Gly Thr Asp Pro Asn Val Ser Gln Asn Leu Pro
        115                 120                 125

Phe Gly Val Met Asp Ser Arg Leu Ile Phe Arg Leu Lys Val Ile Arg
    130                 135                 140

Pro Phe Ile Asn Met Val Glu Ile Pro Arg Gln Val Met Phe Thr Val
145                 150                 155                 160

Tyr Val Thr Ser Thr Pro Tyr Asp Pro Leu Val Thr Pro Val Tyr Thr
            165                 170                 175

Ile Ser Phe Gly Gly Arg Val Glu Val Pro Gln Asn Cys Glu Leu Asn
            180                 185                 190

Ala Gly Gln Ile Val Glu Phe Asp Phe Gly Asp Ile Gly Ala Ser Leu
        195                 200                 205

Phe Ser Ala Ala Gly Pro Gly Asn Arg Pro Ala Gly Val Met Pro Gln
    210                 215                 220

Thr Lys Ser Ile Ala Val Lys Cys Thr Asn Val Ala Ala Gln Ala Tyr
225                 230                 235                 240

Leu Thr Met Arg Leu Glu Ala Ser Ala Val Ser Gly Gln Ala Met Val
            245                 250                 255

Ser Asp Asn Gln Asp Leu Gly Phe Ile Val Ala Asp Gln Asn Asp Thr
```

```
                  260               265                 270
Pro Ile Thr Pro Asn Asp Leu Asn Ser Val Ile Pro Phe Arg Leu Asp
            275                 280                 285

Ala Ala Ala Ala Asn Val Thr Leu Arg Ala Trp Pro Ile Ser Ile
        290                 295                 300

Thr Gly Gln Lys Pro Thr Glu Gly Pro Phe Ser Ala Leu Gly Tyr Leu
305                 310                 315                 320

Arg Val Asp Tyr Gln
                325

<210> SEQ ID NO 9
<211> LENGTH: 516
<212> TYPE: DNA
<213> ORGANISM: Escherichia coli
<220> FEATURE:
<221> NAME/KEY: CDS
<222> LOCATION: (1)..(516)

<400> SEQUENCE: 9 atg aga aga gta ctc ttt agc tgt ttc tgc ggg cta ctg tgg agt tcc      48
Met Arg Arg Val Leu Phe Ser Cys Phe Cys Gly Leu Leu Trp Ser Ser
1               5                  10                  15 agt gga tgg gca gtt gac cct tta gga acg att aat atc aat ttg cac      96
Ser Gly Trp Ala Val Asp Pro Leu Gly Thr Ile Asn Ile Asn Leu His
            20                  25                  30 ggt aac gtt gtt gat ttc tcc tgt acc gta aac aca gcg gat att gat     144
Gly Asn Val Val Asp Phe Ser Cys Thr Val Asn Thr Ala Asp Ile Asp
        35                  40                  45 aag acg gta gat tta ggc aga tgg cct acg aca caa cta ctg aac gct     192
Lys Thr Val Asp Leu Gly Arg Trp Pro Thr Thr Gln Leu Leu Asn Ala
    50                  55                  60 ggc gat acc acg gca ctc gtc cct ttt agc ctg cgg ctg gag gga tgt     240
Gly Asp Thr Thr Ala Leu Val Pro Phe Ser Leu Arg Leu Glu Gly Cys
65                  70                  75                  80 cct ccg ggt tca gtt gcg att tta ttt acg gga acg ccg gca tcc gat     288
Pro Pro Gly Ser Val Ala Ile Leu Phe Thr Gly Thr Pro Ala Ser Asp
                85                  90                  95 acc aac ctg ctg gct ctg gat gat ccc gca atg gca caa acc gtc gcc     336
Thr Asn Leu Leu Ala Leu Asp Asp Pro Ala Met Ala Gln Thr Val Ala
            100                 105                 110 atc gaa tta cgt aat agc gat cgc tcc cgg ctc gca ctg ggg gag gcg     384
Ile Glu Leu Arg Asn Ser Asp Arg Ser Arg Leu Ala Leu Gly Glu Ala
        115                 120                 125 agc ccg act gag gaa gta gat gca aat ggc aat gtc aca cta aac ttt     432
Ser Pro Thr Glu Glu Val Asp Ala Asn Gly Asn Val Thr Leu Asn Phe
    130                 135                 140 ttt gcc aat tat cga gcg tta gcc agc ggt gtt cgg cca ggt gtg gcg     480
Phe Ala Asn Tyr Arg Ala Leu Ala Ser Gly Val Arg Pro Gly Val Ala
145                 150                 155                 160 aaa gcg gat gcg ata ttt atg atc aat tat aat taa                     516
Lys Ala Asp Ala Ile Phe Met Ile Asn Tyr Asn
                165                 170

<210> SEQ ID NO 10
<211> LENGTH: 171
<212> TYPE: PRT
<213> ORGANISM: Escherichia coli

<400> SEQUENCE: 10

Met Arg Arg Val Leu Phe Ser Cys Phe Cys Gly Leu Leu Trp Ser Ser
1               5                  10                  15
```

```
Ser Gly Trp Ala Val Asp Pro Leu Gly Thr Ile Asn Ile Asn Leu His
         20                  25                  30

Gly Asn Val Val Asp Phe Ser Cys Thr Val Asn Thr Ala Asp Ile Asp
             35                  40                  45

Lys Thr Val Asp Leu Gly Arg Trp Pro Thr Thr Gln Leu Leu Asn Ala
 50                  55                  60

Gly Asp Thr Thr Ala Leu Val Pro Phe Ser Leu Arg Leu Glu Gly Cys
 65                  70                  75                  80

Pro Pro Gly Ser Val Ala Ile Leu Phe Thr Gly Thr Pro Ala Ser Asp
                 85                  90                  95

Thr Asn Leu Leu Ala Leu Asp Asp Pro Ala Met Ala Gln Thr Val Ala
                100                 105                 110

Ile Glu Leu Arg Asn Ser Asp Arg Ser Arg Leu Ala Leu Gly Glu Ala
                115                 120                 125

Ser Pro Thr Glu Glu Val Asp Ala Asn Gly Asn Val Thr Leu Asn Phe
            130                 135                 140

Phe Ala Asn Tyr Arg Ala Leu Ala Ser Gly Val Arg Pro Gly Val Ala
145                 150                 155                 160

Lys Ala Asp Ala Ile Phe Met Ile Asn Tyr Asn
                165                 170
```

<210> SEQ ID NO 11
<211> LENGTH: 633
<212> TYPE: DNA
<213> ORGANISM: Escherichia coli
<220> FEATURE:
<221> NAME/KEY: CDS
<222> LOCATION: (1)..(633)

<400> SEQUENCE: 11

```
atg aaa cca acg tcg gtg atc att atg gat act cat cct atc atc aga     48
Met Lys Pro Thr Ser Val Ile Ile Met Asp Thr His Pro Ile Ile Arg
1               5                   10                  15 atg tct att gaa gtt ctg ttg caa aaa aac agt gaa ttg cag att gtc     96
Met Ser Ile Glu Val Leu Leu Gln Lys Asn Ser Glu Leu Gln Ile Val
            20                  25                  30 ctg aaa acg gat gat tat cgc ata acc atc gat tat ctc cga acc cgt    144
Leu Lys Thr Asp Asp Tyr Arg Ile Thr Ile Asp Tyr Leu Arg Thr Arg
        35                  40                  45 cct gtt gat tta atc att atg gat ata gac ttg ccc gga aca gac ggt    192
Pro Val Asp Leu Ile Ile Met Asp Ile Asp Leu Pro Gly Thr Asp Gly
 50                  55                  60 ttt acc ttc ctg aaa agg atc aaa caa atc cag agc aca gtg aaa gtg    240
Phe Thr Phe Leu Lys Arg Ile Lys Gln Ile Gln Ser Thr Val Lys Val
 65                  70                  75                  80 tta ttt tta tca tcg aaa tca gaa tgc ttt tat gct ggc aga gcg ata    288
Leu Phe Leu Ser Ser Lys Ser Glu Cys Phe Tyr Ala Gly Arg Ala Ile
                 85                  90                  95 caa gct ggt gct aac ggt ttt gtc agt aaa tgc aat gat cag aat gat    336
Gln Ala Gly Ala Asn Gly Phe Val Ser Lys Cys Asn Asp Gln Asn Asp
            100                 105                 110 att ttt cat gcc gtt cag atg atc ctc tcc gga tac acg ttt ttt ccc    384
Ile Phe His Ala Val Gln Met Ile Leu Ser Gly Tyr Thr Phe Phe Pro
        115                 120                 125 agc gaa acg ctt aac tat ata aaa agc aat aaa tgt agt acg aat agt    432
Ser Glu Thr Leu Asn Tyr Ile Lys Ser Asn Lys Cys Ser Thr Asn Ser
    130                 135                 140 tca acg gtc act gtg cta tct aat cgt gaa gtg acc ata tta cgt tat    480
Ser Thr Val Thr Val Leu Ser Asn Arg Glu Val Thr Ile Leu Arg Tyr
145                 150                 155                 160
```

```
ctg gtt agc gga tta tct aat aaa gaa att gcc gat aag tta tta ctt     528
Leu Val Ser Gly Leu Ser Asn Lys Glu Ile Ala Asp Lys Leu Leu Leu
            165                 170                 175 agc aat aaa aca gtt agt gcg cat aaa tct aat att tat ggc aag cta     576
Ser Asn Lys Thr Val Ser Ala His Lys Ser Asn Ile Tyr Gly Lys Leu
            180                 185                 190 ggt ttg cat tca att gta gag ctt atc gac tac gcc aaa tta tac gaa     624
Gly Leu His Ser Ile Val Glu Leu Ile Asp Tyr Ala Lys Leu Tyr Glu
            195                 200                 205 tta ata taa                                                         633
Leu Ile
    210

<210> SEQ ID NO 12
<211> LENGTH: 210
<212> TYPE: PRT
<213> ORGANISM: Escherichia coli

<400> SEQUENCE: 12

Met Lys Pro Thr Ser Val Ile Ile Met Asp Thr His Pro Ile Ile Arg
1               5                   10                  15

Met Ser Ile Glu Val Leu Leu Gln Lys Asn Ser Glu Leu Gln Ile Val
                20                  25                  30

Leu Lys Thr Asp Asp Tyr Arg Ile Thr Ile Asp Tyr Leu Arg Thr Arg
            35                  40                  45

Pro Val Asp Leu Ile Ile Met Asp Ile Asp Leu Pro Gly Thr Asp Gly
        50                  55                  60

Phe Thr Phe Leu Lys Arg Ile Lys Gln Ile Gln Ser Thr Val Lys Val
65                  70                  75                  80

Leu Phe Leu Ser Ser Lys Ser Glu Cys Phe Tyr Ala Gly Arg Ala Ile
                85                  90                  95

Gln Ala Gly Ala Asn Gly Phe Val Ser Lys Cys Asn Asp Gln Asn Asp
            100                 105                 110

Ile Phe His Ala Val Gln Met Ile Leu Ser Gly Tyr Thr Phe Phe Pro
        115                 120                 125

Ser Glu Thr Leu Asn Tyr Ile Lys Ser Asn Lys Cys Ser Thr Asn Ser
130                 135                 140

Ser Thr Val Thr Val Leu Ser Asn Arg Glu Val Thr Ile Leu Arg Tyr
145                 150                 155                 160

Leu Val Ser Gly Leu Ser Asn Lys Glu Ile Ala Asp Lys Leu Leu Leu
                165                 170                 175

Ser Asn Lys Thr Val Ser Ala His Lys Ser Asn Ile Tyr Gly Lys Leu
            180                 185                 190

Gly Leu His Ser Ile Val Glu Leu Ile Asp Tyr Ala Lys Leu Tyr Glu
        195                 200                 205

Leu Ile
    210

<210> SEQ ID NO 13
<211> LENGTH: 120
<212> TYPE: DNA
<213> ORGANISM: Artificial
<220> FEATURE:
<223> OTHER INFORMATION: DNA fragment containing attL

<400> SEQUENCE: 13
agatcttgaa gcctgctttt ttatactaag ttggcattat aaaaaagcat tgcttatcaa     60
tttgttgcaa cgaacaggtc actatcagtc aaaataaaat cattatttga tttcgaattc    120
```

```
<210> SEQ ID NO 14
<211> LENGTH: 40
<212> TYPE: DNA
<213> ORGANISM: Artificial
<220> FEATURE:
<223> OTHER INFORMATION: primer P1

<400> SEQUENCE: 14
ctagtaagat cttgaagcct gctttttat actaagttgg                              40

<210> SEQ ID NO 15
<211> LENGTH: 41
<212> TYPE: DNA
<213> ORGANISM: Artificial
<220> FEATURE:
<223> OTHER INFORMATION: primer P2

<400> SEQUENCE: 15
atgatcgaat tcgaaatcaa ataatgattt tattttgact g                           41

<210> SEQ ID NO 16
<211> LENGTH: 184
<212> TYPE: DNA
<213> ORGANISM: Artificial
<220> FEATURE:
<223> OTHER INFORMATION: DNA fragment containing attR

<400> SEQUENCE: 16
ctgcagtctg ttacaggtca ctaataccat ctaagtagtt gattcatagt gactgcatat       60
gttgtgtttt acagtattat gtagtctgtt ttttatgcaa aatctaattt aatatattga     120
tatttatatc attttacgtt tctcgttcag cttttttata ctaacttgag cgtctagaaa     180
gctt                                                                 184

<210> SEQ ID NO 17
<211> LENGTH: 41
<212> TYPE: DNA
<213> ORGANISM: Artificial
<220> FEATURE:
<223> OTHER INFORMATION: primer P3

<400> SEQUENCE: 17
atgccactgc agtctgttac aggtcactaa taccatctaa g                           41

<210> SEQ ID NO 18
<211> LENGTH: 46
<212> TYPE: DNA
<213> ORGANISM: Artificial
<220> FEATURE:
<223> OTHER INFORMATION: primer P4

<400> SEQUENCE: 18
accgttaagc tttctagacg ctcaagttag tataaaaaag ctgaac                      46

<210> SEQ ID NO 19
<211> LENGTH: 38
<212> TYPE: DNA
<213> ORGANISM: Artificial
<220> FEATURE:
<223> OTHER INFORMATION: primer P5

<400> SEQUENCE: 19
ttcttagacg tcaggtggca cttttcgggg aaatgtgc                               38
```

```
<210> SEQ ID NO 20
<211> LENGTH: 37
<212> TYPE: DNA
<213> ORGANISM: Artificial
<220> FEATURE:
<223> OTHER INFORMATION: primer P6

<400> SEQUENCE: 20
taacagagat ctcgcgcaga aaaaaaggat ctcaaga                              37

<210> SEQ ID NO 21
<211> LENGTH: 46
<212> TYPE: DNA
<213> ORGANISM: Artificial
<220> FEATURE:
<223> OTHER INFORMATION: primer P7

<400> SEQUENCE: 21
aacagagatc taagcttaga tcctttgcct ggcggcagta gcgcgg                    46

<210> SEQ ID NO 22
<211> LENGTH: 35
<212> TYPE: DNA
<213> ORGANISM: Artificial
<220> FEATURE:
<223> OTHER INFORMATION: primer P8

<400> SEQUENCE: 22
ataaactgca gcaaaaagag tttgtagaaa cgcaa                                35

<210> SEQ ID NO 23
<211> LENGTH: 1388
<212> TYPE: DNA
<213> ORGANISM: Artificial
<220> FEATURE:
<223> OTHER INFORMATION: DNA fragment containing Tc gene and ter_thrL

<400> SEQUENCE: 23
gaattctcat gtttgacagc ttatcatcga taagctttaa tgcggtagtt tatcacagtt     60
aaattgctaa cgcagtcagg caccgtgtat gaaatctaac aatgcgctca tcgtcatcct    120
cggcaccgtc accctggatg ctgtaggcat aggcttggtt atgccggtac tgccgggcct    180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
```

```
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
actagaaagc ttaacacaga aaaagcccg cacctgacag tgcgggcttt ttttttcgac   1380
cactgcag                                                            1388
```

```
<210> SEQ ID NO 24
<211> LENGTH: 36
<212> TYPE: DNA
<213> ORGANISM: Artificial
<220> FEATURE:
<223> OTHER INFORMATION: primer P9

<400> SEQUENCE: 24
agtaattcta gaaagcttaa cacagaaaaa agcccg                              36
```

```
<210> SEQ ID NO 25
<211> LENGTH: 43
<212> TYPE: DNA
<213> ORGANISM: Artificial
<220> FEATURE:
<223> OTHER INFORMATION: primer P10

<400> SEQUENCE: 25
ctagtaggat ccctgcagtg gtcgaaaaaa aaagcccgca ctg                      43
```

```
<210> SEQ ID NO 26
<211> LENGTH: 1162
<212> TYPE: DNA
<213> ORGANISM: Artificial
<220> FEATURE:
<223> OTHER INFORMATION: DNA fragment containing Pa2 promoter

<400> SEQUENCE: 26
agatctccgg ataagtagac agcctgataa gtcgcacgaa aaacaggtat tgacaacatg   60
aagtaacatg cagtaagata caaatcgcta ggtaacacta gcagcgtcaa ccgggcgctc   120
tagctagagc caagctagct tggccggatc cgagattttc aggagctaag gaagctaaaa   180
tggagaaaaa aatcactgga tataccaccg ttgatatatc ccaatggcat cgtaaagaac   240
attttgaggc atttcagtca gttgctcaat gtacctataa ccagaccgtt cagctggata   300
ttacggcctt tttaaagacc gtaaagaaaa ataagcacaa gttttatccg gcctttattc   360
acattcttgc ccgcctgatg aatgctcatc cggaattccg tatggcaatg aaagacggtg   420
agctggtgat atgggatagt gttcaccctt gttacaccgt tttccatgag caaactgaaa   480
cgttttcatc gctctggagt gaataccacg acgatttccg gcagtttcta cacatatatt   540
cgcaagatgt ggcgtgttac ggtgaaaacc tggcctattt ccctaaaggg tttattgaga   600
atatgttttt cgtctcagcc aatccctggg tgagtttcac cagttttgat ttaaacgtgg   660
ccaatatgga caacttcttc gcccccgttt tcaccatggg caaatattat acgcaaggcg   720
acaaggtgct gatgccgctg gcgattcagg ttcatcatgc cgtctgtgat ggcttccatg   780
tcggcagaat gcttaatgaa ttacaacagt actgcgatga gtggcagggc ggggcgtaat   840
ttttttaagg cagttattgg tgcccttaaa cgcctggtgc tacgcctgaa taagtgataa   900
taagcggatg aatggcagaa attcgtcgaa gcttaacaca gaaaaagcc cgcacctgac   960 agtgcgggct ttttttttcg accactgcag tctgttacag gtcactaata ccatctaagt   1020
```

```
agttgattca tagtgactgc atatgttgtg ttttacagta ttatgtagtc tgtttttat    1080 gcaaaatcta atttaatata ttgatattta tcatttta cgtttctcgt tcagcttttt    1140
tatactaact tgagcgtcta ga                                            1162
```

<210> SEQ ID NO 27
<211> LENGTH: 37
<212> TYPE: DNA
<213> ORGANISM: Artificial
<220> FEATURE:
<223> OTHER INFORMATION: primer P11

<400> SEQUENCE: 27

```
atcgaggtac cagatctccg gataagtaga cagcctg                              37
```

<210> SEQ ID NO 28
<211> LENGTH: 32
<212> TYPE: DNA
<213> ORGANISM: Artificial
<220> FEATURE:
<223> OTHER INFORMATION: primer P12

<400> SEQUENCE: 28

```
gaaggtctag agcgcccggt tgacgctgct ag                                   32
```

<210> SEQ ID NO 29
<211> LENGTH: 27
<212> TYPE: DNA
<213> ORGANISM: Artificial
<220> FEATURE:
<223> OTHER INFORMATION: primer P13

<400> SEQUENCE: 29

```
ctaatatcga tgaagattct tgctcaa                                         27
```

<210> SEQ ID NO 30
<211> LENGTH: 34
<212> TYPE: DNA
<213> ORGANISM: Artificial
<220> FEATURE:
<223> OTHER INFORMATION: primer P14

<400> SEQUENCE: 30

```
gcgttgaatt ccatacaacc tccttagtac atgc                                 34
```

<210> SEQ ID NO 31
<211> LENGTH: 34
<212> TYPE: DNA
<213> ORGANISM: Artificial
<220> FEATURE:
<223> OTHER INFORMATION: primer P15

<400> SEQUENCE: 31

```
gtactagaat tcgtgtaatt gcggagactt tgcg                                 34
```

<210> SEQ ID NO 32
<211> LENGTH: 41
<212> TYPE: DNA
<213> ORGANISM: Artificial
<220> FEATURE:
<223> OTHER INFORMATION: primer P16

<400> SEQUENCE: 32

```
aatagcctgc agttatttga tttcaatttt gtcccactcc c                         41
```

```
<210> SEQ ID NO 33
<211> LENGTH: 57
<212> TYPE: DNA
<213> ORGANISM: Artificial
<220> FEATURE:
<223> OTHER INFORMATION: primer P17

<400> SEQUENCE: 33
aacggaaaat tgtccgctcc tatgagactg gtaacttagt aagccagtat acactcc        57

<210> SEQ ID NO 34
<211> LENGTH: 57
<212> TYPE: DNA
<213> ORGANISM: Artificial
<220> FEATURE:
<223> OTHER INFORMATION: primer P18

<400> SEQUENCE: 34
cagtgtctta ataaagtaa tcggttatat acggatttaa gggcaccaat aactgcc         57

<210> SEQ ID NO 35
<211> LENGTH: 21
<212> TYPE: DNA
<213> ORGANISM: Artificial
<220> FEATURE:
<223> OTHER INFORMATION: primer P19

<400> SEQUENCE: 35
cgtctgaatc aagaaaaccc g                                                21

<210> SEQ ID NO 36
<211> LENGTH: 21
<212> TYPE: DNA
<213> ORGANISM: Artificial
<220> FEATURE:
<223> OTHER INFORMATION: primer P20

<400> SEQUENCE: 36
cgcggaagta ttcatctaac g                                                21

<210> SEQ ID NO 37
<211> LENGTH: 63
<212> TYPE: DNA
<213> ORGANISM: Artificial
<220> FEATURE:
<223> OTHER INFORMATION: primer P21

<400> SEQUENCE: 37
ttatattaat tcgtataatt tggcgtagtc gataagtgaa gcctgctttt ttatactaag     60
ttg                                                                    63

<210> SEQ ID NO 38
<211> LENGTH: 63
<212> TYPE: DNA
<213> ORGANISM: Artificial
<220> FEATURE:
<223> OTHER INFORMATION: primer P22

<400> SEQUENCE: 38
catgtatcaa agtacaattt cccgacctaa cggaaacgct caagttagta taaaaagct      60 gaa                                                                    63

<210> SEQ ID NO 39
<211> LENGTH: 22
<212> TYPE: DNA
<213> ORGANISM: Artificial
```

```
<220> FEATURE:
<223> OTHER INFORMATION: primer P23

<400> SEQUENCE: 39
cgtataattt ggcgtagtcg at                                        22

<210> SEQ ID NO 40
<211> LENGTH: 24
<212> TYPE: DNA
<213> ORGANISM: Artificial
<220> FEATURE:
<223> OTHER INFORMATION: primer P24

<400> SEQUENCE: 40
catgtatcaa agtacaattt cccg                                      24
```

METHOD FOR PRODUCING AN L-AMINO ACID USING A BACTERIUM OF THE ENTEROBACTERIACEAE FAMILY WITH ATTENUATED EXPRESSION OF THE SFMACDFH-FIMZ CLUSTER OR THE FIMZ GENE

This application is a continuation under 35 U.S.C. §120 of PCT Patent Application No. PCT/JP2007/058902, filed on Apr. 18, 2007, which claims priority under 35 U.S.C. §119(a) to Russian Patent Application No. 2006112624, filed on Apr. 18, 2006, and U.S. Provisional Patent Application No. 60/829,923, filed on Oct. 18, 2006, the entireties of which are incorporated by reference. Also, the Sequence Listing filed electronically herewith is hereby incorporated by reference (File name: US-273_Seq_List; File size: 54 KB; Date recorded: Oct. 17, 2008).

BACKGROUND OF THE INVENTION

1. Field of the Invention

The present invention relates to the microbiological industry, and specifically to a method for producing an L-amino acid using a bacterium of the Enterobacteriaceae family which has been modified to attenuate expression of the sfmACDFH-fimZ cluster or the fimZ gene.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170; 5,661,012 and 6,040,160).

Another way to enhance L-amino acid production yields is to attenuate expression of a gene or several genes encoding protein(s) involved in the degradation of the target L-amino acid, the diversion of the precursors of the target L-amino acid from the L-amino acid biosynthetic pathway, and the redistribution of carbon, nitrogen, and phosphate fluxes, and genes encoding toxins etc.

The sfmA gene encodes the SfmA protein, which is a putative fimbrial-like protein. The sfmc gene encodes the SfmC protein, which is a putative shaperone. The sfmD gene encodes the SfmD protein, which is a putative outer membrane protein. The sfmH gene encodes the SfmH protein, which is a putative protein involved fimbrial assembly. The sfmF gene encodes the SfmF protein, which is a putative fimbrial-like protein. The fimZ gene encodes the FimZ protein, which is a putative transcriptional regulator (http://ecocyc.org).

But currently, there have been no reports of attenuating expression of the sfmACDFH-fimZ cluster or the fimZ gene for the purpose of producing L-amino acids.

SUMMARY OF THE INVENTION

The present invention describes enhancing the productivity of L-amino acid-producing strains and providing a method for producing an L-amino acid using these strains.

It was found that by attenuating expression of the sfmACDFH-fimZ cluster or the fimZ gene, production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan can be increased.

The present invention provides a bacterium of the Enterobacteriaceae family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of a gene selected from a group consisting of sfmACDFH-fimZ and fimZ.

It is a further aspect of the present invention to provide the bacterium as described above, wherein the expression is attenuated by inactivation of the gene.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide a method for producing an L-amino acid comprising:

cultivating the bacterium as described above in a medium to produce and excrete said L-amino acid into the medium, and collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1. Bacterium

Figure 1:
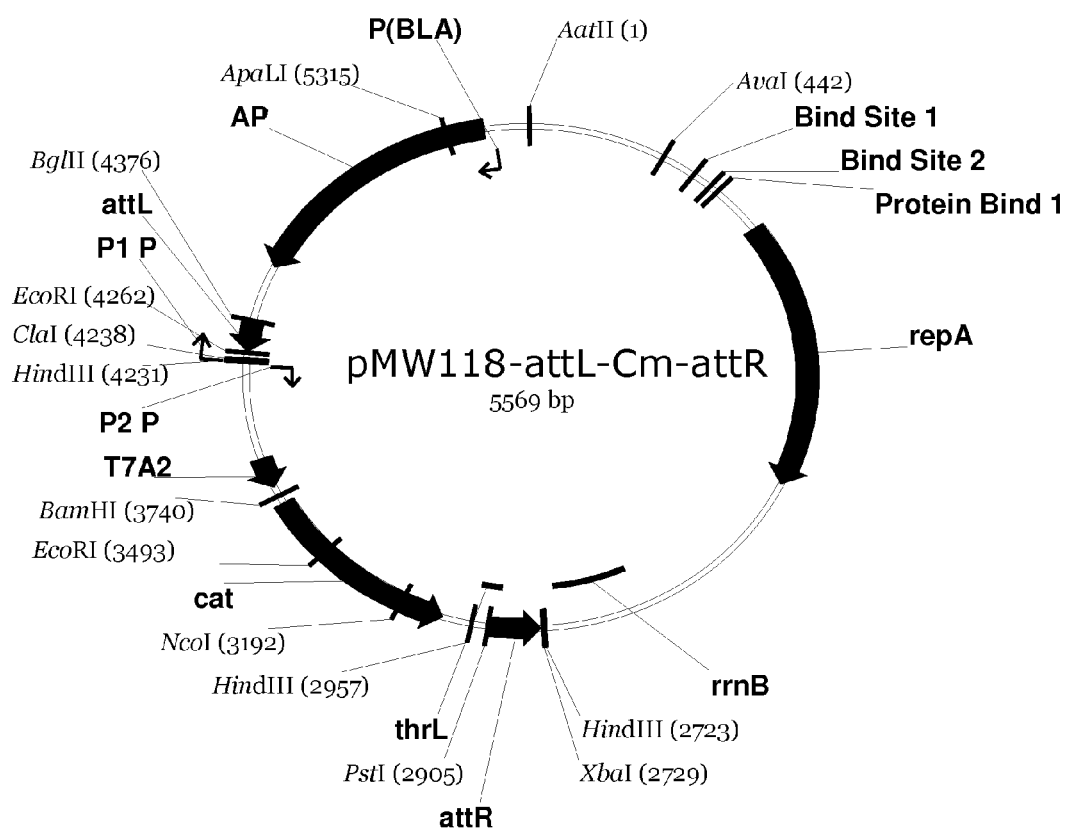
FIG. 1 shows the construction of the pMW118-attL-Cm-attR plasmid, which is used as a template for PCR.

The bacterium is an L-amino acid-producing bacterium of the Enterobacteriaceae family, wherein the bacterium has been modified to attenuate expression of the sfmACDFH-fimZ cluster or the fimZ gene.

The phrase "L-amino acid-producing bacterium" means a bacterium which has an ability to produce and excrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of the bacterium, for example, E. coli, such as E. coli K-12, and preferably means that the bacterium is able to cause accumulation in the medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae according to the taxonomy used by the NCBI (National Center for Biotechnology Information) database (www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of a gene selected from a group consisting of sfmACDFH-fimZ cluster and fimZ gene" means that the bacterium has been modified in such a way that the modified bacterium contains a reduced amount of any of the SfmA, SfmC, SfmD, SfmH, SfmF, and FimZ proteins, as compared with an unmodified bacterium, or is unable to synthesize one of, any combination of, or even all of these proteins. The phrase "bacterium has been modified to attenuate expression of the sfmACDFH-fimZ cluster or the fimZ gene" also means that the target gene is modified in such a way that the modified genes encode a mutant SfmA, SfmC, SfmD, SfmH, SfmF, or FimZ protein which has a decreased activity.

The phrase "inactivation of the gene" means that the modified gene encodes a completely non-functional protein. It is also possible that the modified DNA region is unable to naturally express the gene due to the deletion of a part of the gene or of the gene entirely, the shifting of the reading frame of the gene, the introduction of missense/nonsense mutation(s), or the modification of an adjacent region of the gene, including sequences controlling gene expression, such as promoters, enhancers, attenuators, ribosome-binding sites, etc. The presence or absence of the sfmACDFH-fimZ cluster or the fimZ gene in the chromosome of a bacterium can be detected by well-known methods, including PCR, Southern blotting, and the like. In addition, the level of gene expression can be estimated by measuring the amount of MRNA transcribed from the gene using various known methods including Northern blotting, quantitative RT-PCR, and the like.

The amount of the proteins encoded by the genes of sfmACDFH-fimZ cluster can be measured by well-known methods, including SDS-PAGE followed by immunoblotting assay (Western blotting analysis) and the like.

The sfmACDFH-fimZ cluster includes the sfmACDFH operon and the fimZ gene.

The sfmACDFH operon includes genes in the following order.

The sfmA gene (synonym -b0530) encodes a putative fimbrial-like protein (synonyms-SfmA, B0530). The sfmA gene of *E. coli* (nucleotide positions 557,402 to 557,977; GenBank accession no. NC_000913.2; gi:49175990) is located between the folD and sfmc genes on the chromosome of *E. coli* K-12. The nucleotide sequence of the sfmA gene and the amino acid sequence of SfmA encoded by the sfmA gene are shown in SEQ ID NO: 1 and SEQ ID NO: 2, respectively.

The sfmc gene (synonym—b0531) encodes a putative shaperon (synonyms-SfmC, B0531). The sfmc gene of *E. coli* (nucleotide positions 558,197 to 558,889; GenBank accession no. NC_000913.2; gi:49175990) is located between the sfmA and sfmD genes on the chromosome of *E. coli* K-12. The nucleotide sequence of the sfmc gene and the amino acid sequence of SfmC encoded by the sfmc gene are shown in SEQ ID NO: 3 and SEQ ID NO: 4, respectively.

The sfmD gene (synonym—b0532) encodes a putative outer membrane protein with export function (synonyms-SfmD, B0532). The sfmD gene of *E. coli* (nucleotide positions 558,920 to 561,523; GenBank accession no. NC_000913.2; gi:49175990) is located between the sfmc and sfmH genes on the chromosome of *E. coli* K-12. The nucleotide sequence of the sfmD gene and the amino acid sequence of SfmD encoded by the sfmD gene are shown in SEQ ID NO: 5 and SEQ ID NO: 6, respectively.

The sfmH gene (synonym—b0533) encodes a protein involved in fimbrial assembly (synonyms-SfmH, B0533). The sfmH gene of *E. coli* (nucleotides 561,565 to 562,542; GenBank accession no. NC_000913.2; gi:49175990) is located between the sfmD and sfmF genes on the chromosome of *E. coli* K-12. The nucleotide sequence of the sfmH gene and the amino acid sequence of SfmH encoded by the sfmH gene are shown in SEQ ID NO: 7 and SEQ ID NO: 8, respectively.

The sfmF gene (synonyms—b0534, ybcG) encodes a putative fimbrial-like protein (synonyms—SfmF, B0534, YbcG, ). The sfmF gene of *E. coli* (nucleotides 562,553 to 563,068; GenBank accession no. NC_000913.2; gi:49175990) is located between the sfmH and fimZ genes on the chromosome of *E. coli* K-12. The nucleotide sequence of the sfmF gene and the amino acid sequence of SfmF encoded by the sfmF gene are shown in SEQ ID NO: 9 and SEQ ID NO: 10, respectively.

The fimZ gene (synonyms—b0535, ybcG) encodes a transcriptional regulator(synonyms—FimZ, B0535, YbcA). The fimZ gene of *E. coli* (nucleotides complementary to nucleotides 563,071 to 563,703 GenBank accession no. NC_000913.2; gi:49175990) is located between the sfmF and argU genes on the chromosome of *E. coli* K-12. The nucleotide sequence of the fimZ gene and the amino acid sequence of FimZ encoded by the fimZ gene are shown in SEQ ID NO: 11 and SEQ ID NO: 12, respectively.

Since there may be some differences in DNA sequences between the genera or strains of the Enterobacteriaceae family, the sfmACDFH operon and the fimZ gene to be inactivated on the chromosome are not limited to the genes shown in SEQ ID NOs: 1, 3, 5, 7, 9, and 11, but may include genes homologous to SEQ ID NOs: 1, 3, 5, 7, 9, and 11 which encode variant proteins. The phrase "variant protein" means a protein which has changes in the sequence, whether they are deletions, insertions, additions, or substitutions of amino acids, but still maintains the activity of the protein. The number of changes in the variant protein depends on the position in the three dimensional structure of the protein or the type of amino acid residues. It may be 1 to 30, preferably 1 to 15, and more preferably 1 to 5 in SEQ ID NOs: 2, 4, 6, 8, 10, and 12. These changes in the variants are conservative mutations that preserve the function of the protein. In other words, these changes in the variants can occur in regions of the protein which are not critical for the function of the protein. This is because some amino acids have high homology to one another so the three dimensional structure or activity is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Specific examples of substitutions that are considered to be conservative include: substitution of Ala with Ser or Thr; substitution of Arg with Gln, His, or Lys; substitution of Asn with Glu, Gln, Lys, His, or Asp; substitution of Asp with Asn, Glu, or Gln; substitution of Cys with Ser or Ala; substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu. Substitutions, deletions, insertions, additions, or inversions and the like of the amino acids described above include naturally occurred mutations (mutant or variant) depending on differences in species, or individual differences of microorganisms that retain the ybdA gene. Such a gene can be obtained by modifying the nucleotide sequences shown in SEQ ID NO: 1, 3, 5, 7, 9, and 11 using, for example, site-directed mutagenesis, so that the site-specific amino acid residue in the protein encoded includes substitutions, deletions, insertions, or additions.

Moreover, the protein variants encoded by the sfmACDFH operon and the fimZ gene may have a homology of not less than 80%, preferably not less than 90%, and most preferably not less than 95%, with respect to the entire amino acid sequences shown in SEQ ID NOs. 2, 4, 6, 8, 10, 12 as long as the native activity of SfmA, SfmC, SfmD, SfmH, SfmF and FimZ proteins prior to inactivation are maintained.

Homology between two amino acid sequences can be determined using well-known methods, for example, the computer program BLAST 2.0, which calculates three parameters: score, identity and similarity.

Moreover, genes of the sfmACDFH operon and the fimZ gene may be variants which hybridize under stringent conditions with the nucleotide sequences shown in SEQ ID NOs: 1, 3, 5, 7, 9, and 11 or probes which can be prepared from the nucleotide sequences, provided that functional SfmA, SfmC, SfmD, SfmH, SfmF and FimZ proteins are encoded. "Stringent conditions" include those under which a specific hybrid, for example, a hybrid having homology of not less than 60%, more preferably not less than 70%, further preferably not less than 80%, and still more preferably not less than 90%, and most preferably not less than 95% is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+nylon membrane (Amersham) under stringent conditions is 15 minutes. Preferably, washing may be performed 2 to 3 times. The length of the probe may be suitably selected, depending on the hybridization conditions, and usually varies from 100 bp to 1 kbp.

Expression of the genes of the sfmACDFH operon and/or the fimZ gene can be attenuated by introducing a mutation into the gene on the chromosome so that the intracellular activity of the protein encoded by the gene is decreased as compared to an unmodified strain. Such a mutation can be the replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the genes of the sfmACDFH operon and/or the fimZ gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and a bacterium is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). Furthermore, the incorporation of a site-specific mutation by gene substitution using homologous recombination such as set forth above can also be conducted with a plasmid lacking the ability to replicate in the host.

Expression of the gene can also be attenuated by insertion of a transposon or an IS factor into the coding region of the gene (U.S. Pat. No. 5,175,107), or by conventional methods, such as mutagenesis with UV irradiation or nitrosoguanidine (N-methyl-N'-nitro-N-nitrosoguanidine) treatment.

Inactivation of the gene can be also performed by conventional methods, such as mutagenesis with UV irradiation or nitrosoguanidine (N-methyl-N'-nitro-N-nitrosoguanidine) treatment, site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45) also called "Red-driven integration".

Functional properties are not known for any of the proteins encoded by the sfmA gene, the sfmc gene, the sfmD gene, the sfmH gene, the sfmF gene and the fimZ gene. The presence or absence of the sfmA gene, the sfmc gene, the sfmD gene, the sfmH gene, the sfmF gene or the fimZ gene in the chromosome of a bacterium can be detected by well-known methods, including PCR, Southern blotting, and the like. In addition, the level of gene expression can be estimated by measuring the amount of mRNA transcribed from the sfmA gene, the sfmc gene, the sfmD gene, the sfmH gene, the sfmF gene or the fimZ gene using various well-known methods, including Northern blotting, quantitative RT-PCR, and the like. The amount of the protein encoded by the sfmA gene, the sfmc gene, the sfmD gene, the sfmH gene, the sfmF gene or the fimZ gene can be measured by well-known methods, including SDS-PAGE followed by immunoblotting assay (Western blotting analysis) and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-amino acid-producing bacteria

Bacteria which are modified to attenuate expression of the sfmACDHF-fimZ cluster or the fimZ gene, and which are able to produce either aromatic or non-aromatic L-amino acids may be used.

Such bacteria can be obtained by attenuating expression of the sfmACDHF-fimZ cluster or the fimZ gene in a bacterium which inherently has the ability to produce L-amino acids. Alternatively, the bacterium can be obtained by imparting the ability to produce L-amino acids to a bacterium already having the attenuated expression of the sfmACDHF-fimZ cluster or the fimZ gene.

L-threonine-producing bacteria

Examples of parent strains for deriving the L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No.5,631,157), *E. coli* NRRL-21593 (U.S. Pat. No. 5,939,307), *E. coli* FERM BP-3756 (U.S. Pat. No. 5,474, 918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on November 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow 1, Dorozhny proezd. 1) on Apr. 7, 1987 under the accession number VKPM B-3996.

*E. coli* VKPM B-5318 (EP 0593792B) may also be used as a parent strain for deriving L-threonine-producing bacteria. The strain B-5318 is prototrophic with regard to isoleucine, and a temperature-sensitive lambda-phage Cl repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes:
  the mutant thrA gene which codes for aspartokinase homoserine dehydrogenase I resistant to feed back inhibition by threonine;
  the thrB gene which codes for homoserine kinase;
  the thrC gene which codes for threonine synthase;
  the rhtA gene which codes for a putative transmembrane protein;
  the asd gene which codes for aspartate-β-semialdehyde dehydrogenase; and
  the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from the well-known plasmid pVIC40 which is presented in the threonine producing *E. coli* strain VKPM B-3996. Plasmid pVIC40 is described in detail in U.S. Pat. No. 5,705,371.

The rhtA gene exists at 18 min on the *E. coli* chromosome close to the gInHPQ operon, which encodes components of the glutamine transport system. The rhtA gene is identical to ORFI (ybiF gene, nucleotide positions 764 to 1651, GenBank accession number AAA218541, gi:440181) and is located between the pexB and ompX genes. The unit expressing a protein encoded by the ORFI has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-lysine-producing bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme (WO2005/010175).

L-cysteine-producing bacteria

Examples of parent strains for deriving L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-leucine-producing bacteria

Examples of parent strains for deriving L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403,342). In addition, the bacterium may be improved by enhancing the expression of one or more genes coding for proteins which excrete L-amino acid from the bacterial cell. Examples of such genes include the b2682 and b2683 genes (ygaZH genes) (EP 1239041 A2).

L-histidine-producing bacteria

Examples of parent strains for deriving L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* A180/pFM201 (U.S. Pat. No. 6,258,554) and the like.

Examples of parent strains for deriving L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM P-5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-glutamic acid-producing bacteria

Examples of parent strains for deriving L-glutamic acid-producing bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961), which is able to produce L-glutamic acid, was obtained.

Examples of parent strains for deriving the L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/aor the glutamate dehydrogenase gene is/are enhanced include those disclosed in EP1078989A, EP955368A, and EP952221A.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::KmR is a strain obtained by disrupting the α-ketoglutarate dehydrogenase gene (hereinafter referred to as "sucA gene") of *E. coli* W3110. This strain is completely deficient in the α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-phenylalanine-producing bacteria

Examples of parent strains for deriving L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC10-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-tryptophan-producing bacteria

Examples of parent strains for deriving the L-tryptophan-producing bacteria include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parent strains for deriving the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-proline-producing bacteria

Examples of parent strains for deriving L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium may be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-arginine-producing bacteria

Examples of parent strains for deriving L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-valine-producing bacteria

Example of parent strains for deriving L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parent strains for deriving L-valine-producing bacteria include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-isoleucine-producing bacteria

Examples of parent strains for deriving L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method

A method is described for producing an L-amino acid by cultivating the bacterium as described above in a culture medium to produce and excrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Preparation of the PCR Template and Helper Plasmids

The PCR template plasmid pMW118-attL-Cm-attR and the helper plasmid pMW-intxis-ts were prepared as follows:
(1) pMW118-attL-Cm-attR The pMW118-attL-Cm-attR plasmid was constructed on the basis of pMW118-attL-Tc-attR that was obtained by ligation of the following four DNA fragments:
1) the BglII-EcoRI fragment (114 bp) carrying attL (SEQ ID NO: 13) which was obtained by PCR amplification of the corresponding region of the *E. coli* W3350 (contained λ prophage) chromosome using oligonucleotides P1 and P2 (SEQ ID NOS: 14 and 15) as primers (these primers contained the subsidiary recognition sites for BglII and EcoRI endonucleases);
2) the PstI-HindIII fragment (182 bp) carrying attR (SEQ ID NO: 16) which was obtained by PCR amplification of the corresponding region of the *E. coli* W3350 (contained λ prophage) chromosome using the oligonucleotides P3 and P4 (SEQ ID NOS: 17 and 18) as primers (these primers contained the subsidiary recognition sites for PstI and HindIII endonucleases);
3) the large BglII-HindIII fragment (3916 bp) of pMW118-ter_rrnB. The plasmid pMW118-ter_rrnB was obtained by ligation of the following three DNA fragments:
the large DNA fragment (2359 bp) carrying the AatII-EcoRI fragment of pMW118 that was obtained in the following way: pMW118 was digested with EcoRI restriction endonuclease, treated with Klenow fragment of DNA polymerase I, and then digested with AatII restriction endonuclease;
the small AatII-BglII fragment (1194 bp) of pUC19 carrying the bla gene for ampicillin resistance (Ap$^R$) was obtained by PCR amplification of the corresponding region of the pUC19 plasmid using oligonucleotides P5 and P6 (SEQ ID NOS: 19 and 20) as primers (these primers contained the subsidiary recognition sites for AatII and BglII endonucleases);
the small BglII-PstIpol fragment (363 bp) of the transcription terminator ter_rrnB was obtained by PCR amplification of the corresponding region of the *E. coli* MG1655 chromosome using oligonucleotides P7 and P8 (SEQ ID NOS: 21 and 22) as primers (these primers contained the subsidiary recognition sites for BglII and PstI endonucleases);
4) the small EcoRI-PstI fragment (1388 bp) (SEQ ID NO:23) of pML-Tc-ter_thrL bearing the tetracycline resistance gene and the ter_thrL transcription terminator; the pML-Tc-ter_thrL plasmid was obtained in two steps:
the pML-ter_thrL plasmid was obtained by digesting the pML-MCS plasmid (Mashko, S. V. et al., Biotekhnologiya (in Russian), 2001, no. 5, 3-20) with the XbaI and BamHI restriction endonucleases, followed by ligation of the large fragment (3342 bp) with the XbaI-BamHI fragment (68 bp) carrying terminator ter_thrL obtained by PCR amplification of the corresponding region of the *E. coli* MG1655 chromosome using oligonucleotides P9 and P10 (SEQ ID NOS: 24 and 25) as primers (these primers contained the subsidiary recognition sites for the XbaI and BamHI endonucleases);
the pML-Tc-ter_thrL plasmid was obtained by digesting the pML-ter_thrL plasmid with the KpnI and XbaI restriction endonucleases followed by treatment with Klenow fragment of DNA polymerase I and ligation with the small EcoRI-Van91I fragment (1317 bp) of pBR322 bearing the tetracycline resistance gene (pBR322 was digested with EcoRI and Van91I restriction endonucleases and then treated with Klenow fragment of DNA polymerase I).

The above *E. coli* W3350 is a derivative of wild-type strain *E. coli* K-12. The *E. coli* MG1655 (ATCC 700926) is a wild-type strain and can be obtained from American Type Culture Collection (P.O. Box 1549 Manassas, Va. 20108, United States of America). The plasmids pMW118 and pUC19 are commercially available. The BglII-EcoRI fragment carrying attL and the BglII-PstI fragment of the transcription terminator ter_rrnB can be obtained from other strains of *E. coli* in the same manner as described above.

The pMW118-attL-Cm-attR plasmid was constructed by ligation of the large BamHI-XbaI fragment (4413 bp) of pMW118-attL-Tc-attR and the artificial DNA BglII-XbaI fragment (1162 bp) containing the PA2 promoter (the early promoter of the phage T7), the cat gene for chloramphenicol resistance ($Cm^R$), the ter_thrL transcription terminator, and attR. The artificial DNA fragment (SEQ ID NO:26) was obtained as follows:

1. The pML-MCS plasmid was digested with the KpnI and XbaI restriction endonucleases and ligated with the small KpnI-XbaI fragment (120 bp), which included the PA2 promoter (the early promoter of phage T7) obtained by PCR amplification of the corresponding DNA region of phage T7 using oligonucleotides P11 and P12 (SEQ ID NOS: 27 and 28, respectively) as primers (these primers contained the subsidiary recognition sites for KpnI and XbaI endonucleases). As a result, the pML-$P_{A2}$-MCS plasmid was obtained. The complete nucleotide sequence of phage T7 has been reported (J. Mol. Biol., 166: 477-535 (1983).
2. The XbaI site was deleted from pML-$P_{A2}$-MCS. As a result, the pML-$P_{A2}$-MCS(XbaI$^-$) plasmid was obtained.
3. The small BglII-HindIII fragment (928 bp) of pML-$P_{A2}$-MCS(XbaI$^-$) containing the PA2 promoter (the early promoter of the phage T7) and the cat gene for chloramphenicol resistance ($Cm^R$) was ligated with the small HindIII-HindIII fragment (234 bp) of pMW118-attL-Tc-attR containing the ter_thrL transcription terminator and attR.
4. The required artificial DNA fragment (1156 bp) was obtained by PCR amplification of the ligation reaction mixture using oligonucleotides P9 and P4 (SEQ ID NOS: 24 and 18) as primers (these primers contained the subsidiary recognition sites for HindIII and XbaI endonucleases).

(2) pMW-intxis-ts

Recombinant plasmid pMW-intxis-ts containing the cI repressor gene and the int-xis genes of phage λ under control of promoter $P_R$ was constructed on the basis of vector pMW-$P_{lac}$lacI-ts. To construct the pMWP$_{lac}$lacI-ts variant, the AatII-EcoRV fragment of the pMWP$_{lac}$lacI plasmid (Skorokhodova, A. Yu. et al., Biotekhnologiya (in Russian), 2004, no. 5, 3-21) was substituted with the AatII-EcoRV fragment of the pMAN997 plasmid (Tanaka, K. et al., J. Bacteriol., 2001, 183(22): 6538-6542, WO99/03988) bearing the par and ori loci and the repA$^{ts}$ gene (a temperature sensitive-replication origin) of the pSC101 replicon. The plasmid pMAN997 was constructed by exchanging the VspI-HindIII fragments of pMAN031 (J. Bacteriol., 162, 1196 (1985)) and pUC19.

Two DNA fragments were amplified using phage λ DNA ("Fermentas") as a template. The first one contained the DNA sequence from 37,168 to 38,046, the cI repressor gene, promoters $P_{RM}$ and $P_R$, and the leader sequence of the cro gene. This fragment was PCR-amplified using oligonucleotides P13 and P14 (SEQ ID NOS: 29 and 30) as primers. The second DNA fragment containing the xis-int genes of phage λ and the DNA sequence from 27801 to 29100 was PCR-amplified using oligonucleotides P15 and P16 (SEQ ID NOS: 31 and 32) as primers. All primers contained the corresponding restriction sites.

The first PCR-amplified fragment carrying the cI repressor was digested with restriction endonuclease ClaI, treated with Klenow fragment of DNA polymerase I, and then digested with restriction endonuclease EcoRI. The second PCR-amplified fragment was digested with restriction endonucleases EcoRI and PstI. The pMWP$_{lac}$lacI-ts plasmid was digested with the BglII endonuclease, treated with Klenow fragment of DNA polymerase I, and digested with the PstI restriction endonuclease. The vector fragment of pMWPlaclacI-ts was eluted from agarose gel and ligated with the above-mentioned digested PCR-amplified fragments to obtain the pMW-intxis-ts recombinant plasmid.

Example 2

Construction of a Strain with the Inactivated sfmACDHF-fimZ Cluster

1. Deletion of the sfmACDHF-fimZ Cluster

A strain with the sfmACDHF-fimZ cluster deleted was constructed by the method initially developed by Datsenko, K. A. and Wanner, B. L. (Proc. Natl. Acad. Sci. USA, 2000, 97(12): 6640-6645) called "Red-driven integration". According to this procedure, the PCR primers P17 (SEQ ID NO: 33) and P18 (SEQ ID NO:34), which are complementary to both the region adjacent to the sfmACDHF-fimZ cluster and the gene conferring antibiotic resistance in the template plasmid, were constructed. The plasmid pACYC184 (NBL Gene Sciences Ltd., UK) (GenBank/EMBL accession number X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

Figure 2:
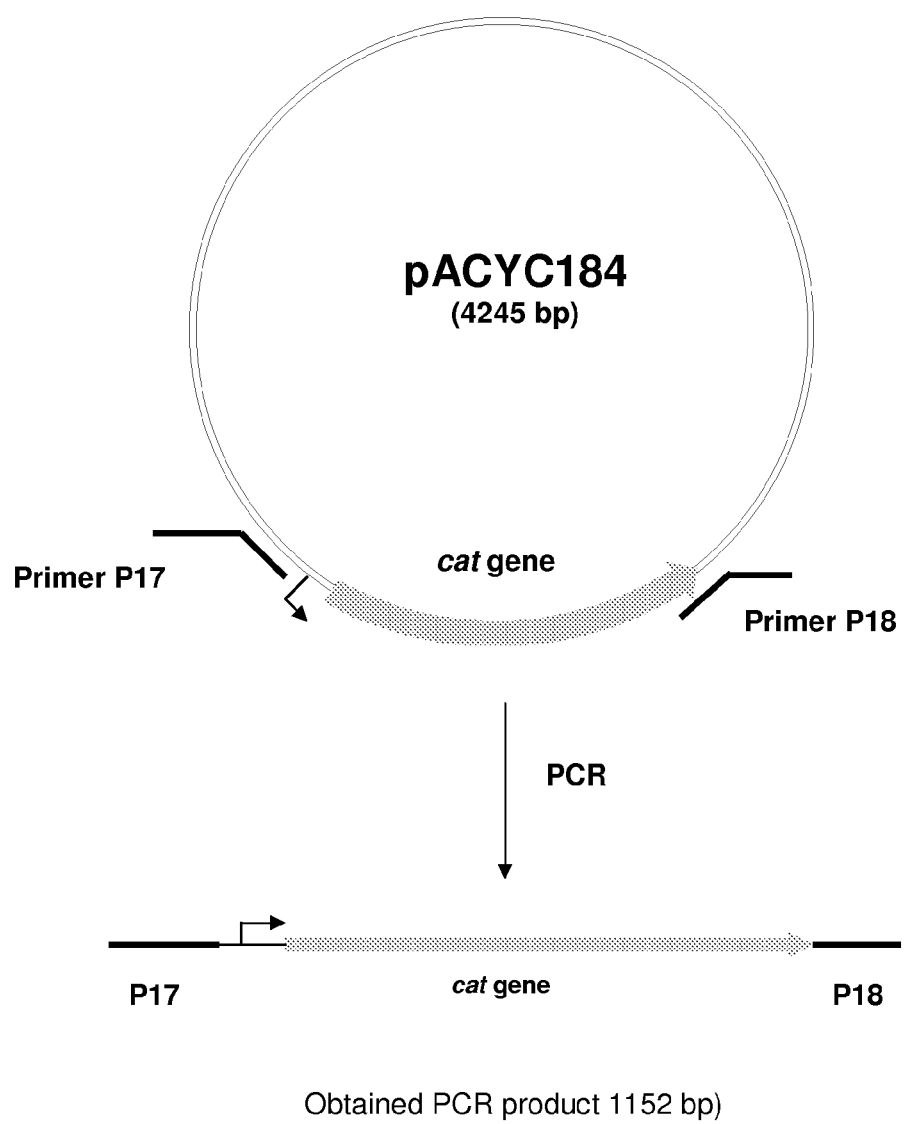
FIG. 2 shows the relative positions of primers P17 and P18 on plasmid pACYC184, which is used for PCR amplification of the cat gene.

A 1152-bp PCR product (FIG. 2) was obtained and purified in agarose gel and was used for electroporation of *E. coli* MG1655 (ATCC 700926), which contains the pKD46 plasmid having temperature-sensitive replication. The pKD46 plasmid (Datsenko, K. A. and Wanner, B. L., Proc. Natl. Acad. Sci. USA, 2000, 97(12):6640-6645) includes a 2,154-bp DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, U.S.A.).

Electrocompetent cells were prepared as follows: *E. coli* MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≠0.6 and then were made electrocompetent by concentrating 100-fold and washing three times with ice-cold deionized $H_2O$. Electroporation was performed using 70 μl of cells and 100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 μg/ml) and grown at 37° C. to select $Cm^R$ recombinants. Then, to eliminate the pKD46 plasmid, two passages on L-agar with Cm at 42° C. were performed and the colonies were tested for sensitivity to ampicillin.

2. Verification of the sfmACDHF-fimZ Cluster Deletion by PCR

Figure 4:
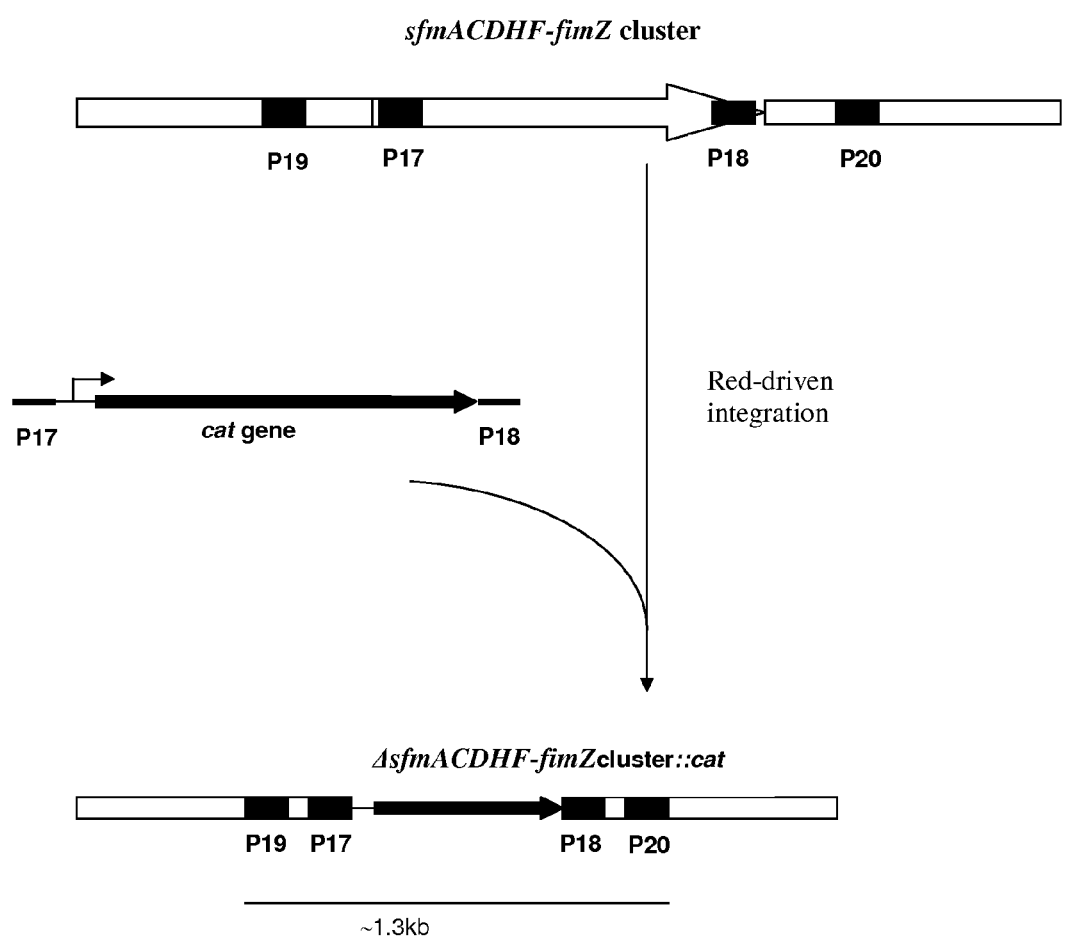
FIG. 4 shows the construction of the chromosomal DNA fragment containing the inactivated sfmACDHF-fimZ cluster.

The mutants having the sfmACDHF-fimZ cluster deleted and marked with the Cm resistance gene were verified by PCR. Locus-specific primers P19 (SEQ ID NO:35) and P20 (SEQ ID NO:36) were used in PCR for the verification. Conditions for PCR verification were as follows: denaturation step: 3 min at 94° C.; profile for 30 cycles: 30 sec at 94° C., 30 sec at 54° C., 1 min at 72° C.; final step: 7 min at 72° C. The PCR product obtained in the reaction with the parental sfmACDHF-fimZ$^+$ MG1655 strain as the template was 6528 bp in length. The PCR product obtained in the reaction with the mutant strain as the template was 1306 bp in length (FIG. 4). The mutant strain was named MG1655 ΔsfmACDHF-fimZ::cat.

Example 3

Production of L-threonine by E. coli Strain B-3996-ΔsfmACDHF-fimZ

To test the effect of inactivation of the sfmACDHF-fimZ cluster on threonine production, DNA fragments from the chromosome of the above-described E. coli MG1655 ΔsfmACDHF-fimZ::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain strain B-3996-ΔsfmACDHF-fimZ.

Both E. coli strains, B-3996 and B-3996-ΔsfmACDHF-fimZ, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium, was determined by paper chromatography using the following mobile phase: butanol—acetic acid—water=4:1:1 (v/v). A solution of ninhydrin (2%) in acetone was used as a visualizing reagent. A spot containing L-threonine was cut out, L-threonine was eluted with 0.5% water solution of $CdCl_2$, and the amount of L-threonine was estimated spectrophotometrically at 540 nm. The results of eight independent test tube fermentations are shown in Table 1. As follows from Table 1, B-3996-ΔsfmACDHF-fimZ caused accumulation of a higher amount of L-threonine, as compared with B-3996.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| ThiamineHCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was introduced into the medium after sterilization.

TABLE 1

| Strain | $OD_{540}$ | Amount of L-threonine, g/l |
|---|---|---|
| B-3996 | 21.6 ± 1.1 | 21.2 ± 0.2 |
| B-3996-ΔsfmACDHF-fimZ | 25.2 ± 0.2 | 21.6 ± 0.4 |

Example 4

Production of L-lysine by E. coli AJ11442-ΔsfmACDHF-fimZ

To test the effect of inactivation of the sfmACDHF-fimZ cluster on lysine production, DNA fragments from the chromosome of the above-described E. coli strain MG1655 ΔsfmACDHF-fimZ::cat can be transferred to the lysine-producing E. coli strain AJ11442 by P1 transduction (Miller, J. H. Experiments in Molecular Genetics, Cold Spring Harbor Lab. Press, 1972, Plainview, N.Y.) to obtain strain AJ11442-ΔsfmACDHF-fimZ. The strain AJ14442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both E. coli strains, AJ11442 and AJ11442-ΔsfmACDHF-fimZ can be cultured in L-medium at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and $MgSO_4$ $7H_2O$ are sterilized separately. $CaCO_3$ is dry-heat sterilized at 180° C. for 2 hours and added to the medium for a final concentration of 30 g/l.

Example 5

Production of L-cysteine by E. coli JM15(ydeD)-ΔsfmACDHF-fimZ

To test the effect of inactivation of the sfmACDHF-fimZ cluster on L-cysteine production, DNA fragments from the chromosome of the above-described E. coli MG1655 ΔsfmACDHF-fimZ::cat can be transferred to the E. coli L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-ΔsfmACDHF-fimZ.

E. coli JM15(ydeD) is a derivative of E. coli JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC# 5042) can be obtained from The Coli Genetic Stock Collection at the E. coli Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 6

Production of L-leucine by E. coli 57-ΔsfmACDHF-fimZ

To test the effect of inactivation of the sfmACDHF-fimZ cluster on L-leucine production, DNA fragments from the chromosome of the above-described E. coli strain MG1655 ΔsfmACDHF-fimZ::cat can be transferred to the E. coli L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-pMWΔsfmACDHF-fimZ strain. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both E. coli strains, 57 and 57-ΔsfmACDHF-fimZ, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol—acetic acid—water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 7

Production of L-histidine by E. coli 80-ΔsfmACDHF-fimZ

To test the effect of inactivation of the sfmACDHF-fimZ cluster on L-histidine production, DNA fragments from the chromosome of the above-described E. coli MG1655 ΔsfmACDHF-fimZ::cat can be transferred to the histidine-producing E. coli strain 80 by P1 transduction (Miller, J. H. Experiments in Molecular Genetics, Cold Spring Harbor Lab. Press, 1972, Plainview, N.Y.) to obtain strain 80-ΔsfmACDHF-fimZ. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both E. coli strains, 80 and 80-ΔsfmACDHF-fimZ, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 8

Production of L-glutamate by E. coli VL334thrC⁺-ΔsfmACDHF-fimZ

To test the effect of inactivation of the sfmACDHF-fimZ cluster on L-glutamate production, DNA fragments from the chromosome of the above-described *E. coli* strain MG1655 ΔsfmACDHF-fimZ::cat can be transferred to the *E. coli* L-glutamate-producing strain VL334thrC⁺ (EP 1172433) by P1 transduction (Miller, J. H. Experiments in Molecular Genetics, Cold Spring Harbor Lab. Press, 1972, Plainview, N.Y.) to obtain the strain VL334thrC⁺-ΔsfmACDHF-fimZ. The strain VL334thrC⁺ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC⁺ and VL334thrC⁺-ΔsfmACDHF-fimZ, can be grown for 18-24 hours at 37° C. on L-agar plates. Then, one loop of the cells can be transferred into test tubes containing 2 ml of fermentation medium. The fermentation medium contains glucose (60g/l), ammonium sulfate (25 g/l), $KH_2PO_4$ (2g/l), $MgSO_4$ (1 g/l), thiamine (0.1 mg/ml), L-isoleucine (70 µg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 9

Production of L-phenylalanine by E. coli AJ12739-ΔsfmACDHF-fimZ

To test the effect of inactivation of the ΔsfmACDHF-fimZ cluster on L-phenylalanine production, DNA fragments from the chromosome of the above-described *E. coli* MG1655 ΔsfmACDHF-fimZ::cat can be transferred to the phenylalanine-producing *E. coli* strain AJ12739 by P1 transduction (Miller, J. H. Experiments in Molecular Genetics, Cold Spring Harbor Lab. Press, 1972, Plainview, N.Y.) to obtain strain AJ12739-ΔsfmACDHF-fimZ. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Both strains, AJ12739-ΔsfmACDHF-fimZ and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol: ethylacetate: 25% aqueous ammonia: water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 10

Production of L-tryptophan by E. coli SV164 (pGH5)-ΔsfmACDHF-fimZ

To test the effect of inactivation of the sfmACDHF-fimZ cluster on L-tryptophan production, DNA fragments from the chromosome of the above-described *E. coli* strain MG1655 ΔsfmACDHF-fimZ::cat can be transferred to the tryptophan-producing *E. coli* strain SV164 (pGH5) by P1 transduction (Miller, J. H. Experiments in Molecular Genetics, Cold Spring Harbor Lab. Press, 1972, Plainview, N.Y.) to obtain the strain SV164(pGH5)-ΔsfmACDHF-fimZ. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143.

Both strains, SV164(pGH5)-ΔsfmACDHF-fimZ and SV164(pGH5), can be cultivated with shaking at 37° C. for 18 hours in 3 ml of nutrient broth supplemented with tetracycline (20 mg/l, marker of pGH5 plasmid). The obtained cultures (0.3 ml each) can be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 2, but should be sterilized in separate groups (A, B, C, D, E, F, and H), as shown, to avoid adverse interactions during sterilization.

TABLE 2

| Groups | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |

TABLE 2-continued

| Groups | Component | Final concentration, g/l |
|---|---|---|
| E | $Na_2MoO_4 \cdot 2H_2O$ | 0.00015 |
|   | $H_3BO_3$ | 0.0025 |
|   | $CoCl_2 \cdot 6H_2O$ | 0.00007 |
|   | $CuSO_4 5H_2O$ | 0.00025 |
|   | $MnCl_2 \cdot 4H_2O$ | 0.0016 |
|   | $ZnSO_4 \cdot 7H_2O$ | 0.0003 |
| F | Thiamine HCl | 0.005 |
| G | $CaCO_3$ | 30.0 |
| H | Pyridoxine | 0.03 |

Group A had pH 7.1 adjusted by $NH_4OH$. Each group is sterilized separately, chilled and then mixed together Example 11

Production of L-proline by *E. coli* 702ilvA-ΔsfmACDHF-fimZ

To test the effect of inactivation of the sfmACDHF-fimZ cluster on L-proline production, DNA fragments from the chromosome of the above-described *E. coli* strain MG1655 ΔsfmACDHF-fimZ::cat can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain strain 702ilvA-ΔsfmACDHF-fimZ. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both *E. coli* strains, 702ilvA and 702ilvA-ΔsfmACDHF-fimZ, can be grown for 18-24 hours at 37° C. on L-agar plates. Then, these strains can be cultivated under the same conditions as in Example 8.

Example 12

Production of L-arginine by *E. coli* 382-ΔsfmACDHF-fimZ

To test the effect of inactivation of the sfmACDHF-fimZ cluster on L-arginine production, DNA fragments from the chromosome of the above-described *E. coli* strain MG1655 ΔsfmACDHF-fimZ::cat can be transferred to the arginine-producing *E. coli* strain 382 by P1 transduction (Miller, J. H. Experiments in Molecular Genetics, Cold Spring Harbor Lab. Press, 1972, Plainview, N.Y.) to obtain strain 382-ΔsfmACDHF-fimZ. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382-ΔsfmACDHF-fimZ and 382, can be cultivated with shaking at 37° C. for 18 hours in 3 ml of nutrient broth, and 0.3 ml of the obtained cultures can be inoculated into 3 ml of a fermentation medium in 20×200-mm test tubes and cultivated at 32° C. for 48 hours on a rotary shaker.

After the cultivation, the amount of L-arginine which accumulates in the medium can be determined by paper chromatography using the following mobile phase:butanol:acetic acid:water=4:1:1 (v/v). A solution of ninhydrin (2%) in acetone can be used as a visualizing reagent. A spot containing L-arginine can be cut out, L-arginine can be eluted with 0.5% water solution of $CdCl_2$, and the amount of L-arginine can be estimated spectrophotometrically at 540 nm.

The composition of the fermentation medium (g/l) is as follows:

| | |
|---|---|
| Glucose | 48.0 |
| $(NH4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

Example 13

Construction of a Strain with the Inactivated fimZ Gene

1. Deletion of the fimZ Gene

A strain with the fimZ gene deleted was constructed by the method initially developed by Datsenko, K. A. and Wanner, B. L. (Proc. Natl. Acad. Sci. USA, 2000, 97(12) 6640-6645) called "Red-driven integration". The DNA fragment containing the $Cm^R$ marker encoded by the cat gene was obtained by PCR, using primers P21 (SEQ ID NO:37) and P22 (SEQ ID NO:38) and plasmid pMW118-attL-Cm-attR as a template (for construction see Example 1). Primer P21 contains both a region complementary to the 36-nt region located at the 5' end of the fimZ gene and a region complementary to the attL region. Primer P22 contains both a region complementary to the 36-nt region located at the 3' end of the fimZ gene and a region complementary to the attR region. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

Figure 3:
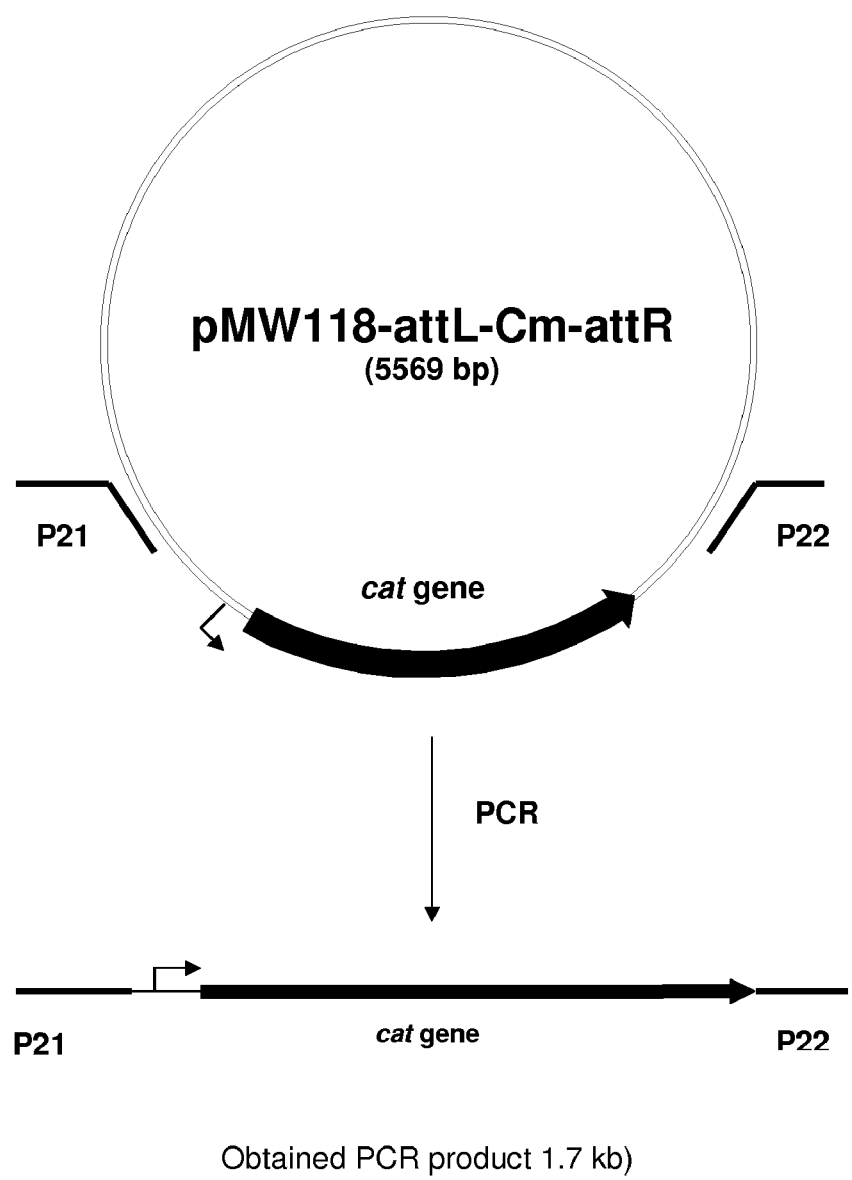
FIG. 3 shows the relative positions of primers P21 and P22 on plasmid pMW118-attL-Cm-attR, which is used for PCR amplification of the cat gene.

A 1.7 kbp PCR product (FIG. 3) was obtained and purified in agarose gel and was used for electroporation of *E. coli* MG1655 (ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97(12) 6640-6645) includes a 2,154-bp DNA fragment of phage λ (nucleotide positions 31088 to 33241, GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells were prepared as described in the Example 2. Electroporation was performed using 70 μl of cells and ≠100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and after that were plated onto L-agar containing chloramphenicol (30 μg/ml) and grown at 37° C. to select $Cm^R$ recombinants. Then, to eliminate the pKD46 plasmid, two passages on L-agar with Cm at 42° C. were performed and the obtained colonies were tested for sensitivity to ampicillin.

2. Verification of the fimZ Gene Deletion by PCR

Figure 5:
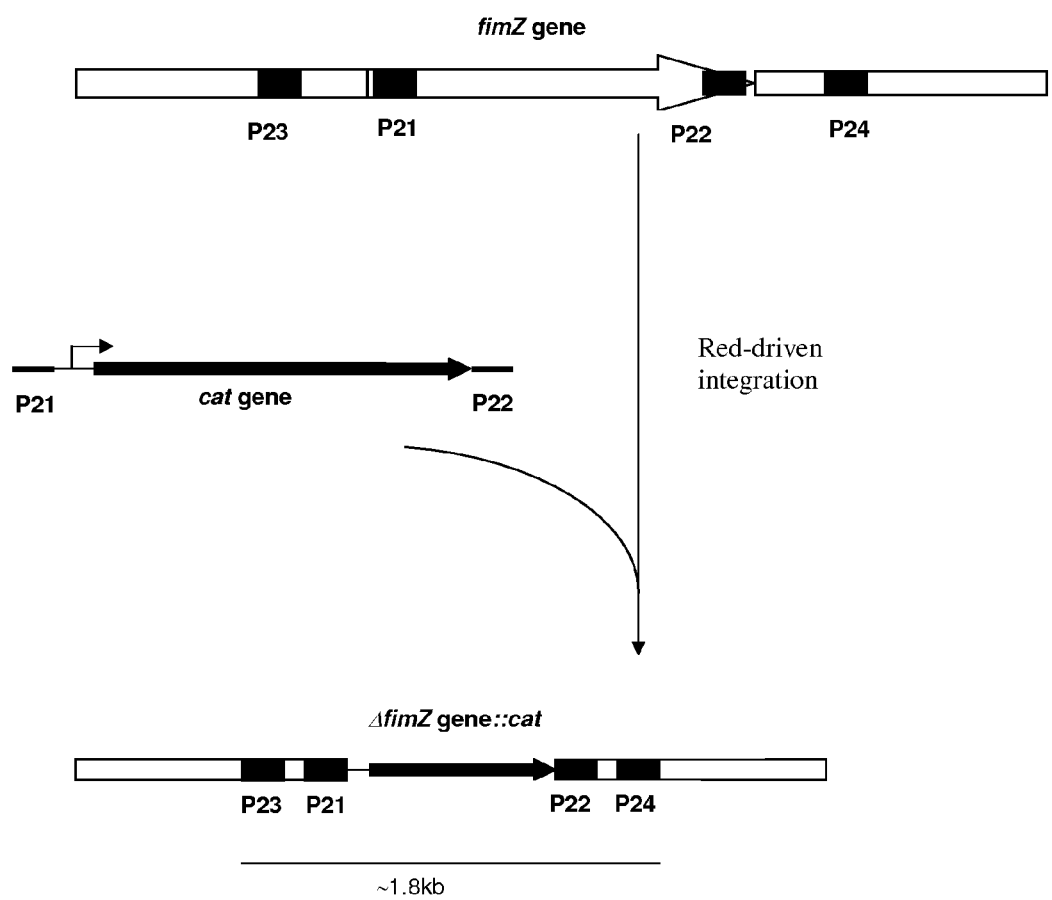
FIG. 5 shows the construction of the chromosomal DNA fragment containing the inactivated fimZ gene.

The mutants, which have the fimZ gene deleted and are marked with the Cm resistance gene, were verified by PCR. Locus-specific primers P23 (SEQ ID NO:39) and P24 (SEQ ID NO:40) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained in the reaction with the cells of the parental strain fimZ$^+$ MG1655 strain as the template was ~0.7 kb in length. The PCR product obtained in the reaction with the cells of the mutant strain as the template was ~1.8 kb in length (FIG. 5). The mutant strain was named MG1655 ΔfimZ::cat.

Example 14

Production of L-threonine by *E. coli* B-3996-ΔfimZ

To test the effect of inactivation of the fimZ gene on threonine production, DNA fragments from the chromosome of the above-described *E. coli* MG1655 ΔfimZ::cat were transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain the strain B-3996-ΔfimZ.

Both *E. coli* B-3996 and B-3996-ΔfimZ, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine which had accumulated in the medium, was determined by paper chromatography using the following mobile phase: butanol:acetic acid:water=4:1:1 (v/v). A solution 2% of ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results of eight independent test tube fermentations are shown in Table 3. As follows from Table 3, B-3996-ΔfimZ caused accumulation of a higher amount of L-threonine, as compared with B-3996.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. The antibiotic was introduced into the medium after sterilization.

TABLE 3

| Strain | $OD_{540}$ | Amount of L-threonine, g/l |
|---|---|---|
| B-3996 | 24.4 ± 0.4 | 26.8 ± 0.5 |
| B-3996-ΔfimZ | 25.4 ± 0.9 | 28.9 ± 0.4 |

Example 15

Production of L-lysine by *E. coli* AJ11442-ΔfimZ

To test the effect of inactivation of the fimZ gene on lysine production, DNA fragments from the chromosome of the above-described *E. coli* strain MG1655 ΔfimZ::cat can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain strain AJ11442-ΔfimZ.

Both *E. coli* strains AJ11442 and AJ11442-ΔfimZ can be cultured in L-medium containing streptomycin (20 mg/l) at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and $MgSO_4 \times 7H_2O$ are sterilized separately. $CaCO_3$ is dry-heat sterilized at 180° C. for 2 hours and added to the medium for a final concentration of 30 g/l.

Example 16

Production of L-cysteine by *E. coli* JM15(ydeD)-ΔfimZ

To test the effect of inactivation of the fimZ gene on L-cysteine production, DNA fragments from the chromosome of the above-described *E. coli* MG1655 ΔfimZ::cat can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD)-ΔfimZ.

*E. coli* JM15(ydeD) is a derivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC# 5042)

can be obtained from The Coli Genetic Stock Collection at the E. coli Genetic Resource Center, MCD Biology Department, Yale University (http://cgsc.biology.yale.edu/).

Fermentation conditions for evaluation of L-cysteine production were described in detail in Example 6 of U.S. Pat. No. 6,218,168.

Example 17

Production of L-leucine by E. coli 57-ΔfimZ

To test the effect of inactivation of the fimZ gene on L-leucine production, DNA fragments from the chromosome of the above-described E. coli strain MG1655 Δ-fimZ::cat can be transferred to the E. coli L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-ΔfimZ.

Both E. coli strains, 57 and 57-ΔfimZ, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol—acetic acid—water=4:1:1).

The composition of the fermentation medium (g/l) (pH 7.2) is as follows:

| | |
|---|---|
| Glucose | 60.0 |
| $(NH_4)_2SO_4$ | 5.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 18

Production of L-histidine by E. coli 80-ΔfimZ

To test the effect of inactivation of the fimZ gene on L-histidine production, DNA fragments from the chromosome of the above-described E. coli MG1655 ΔfimZ::cat can be transferred to the histidine-producing E. coli strain 80 by P1 transduction (Miller, J. H. Experiments in Molecular Genetics, Cold Spring Harbor Lab. Press, 1972, Plainview, N.Y.) to obtain strain 80-ΔfimZ.

Both E. coli strains, 80 and 80-ΔfimZ, can each be cultured in L-broth for 6 h at 29° C. Then, 0.1 ml of obtained culture can each be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 19

Production of L-glutamate by E. coli VL334thrC$^+$-ΔfimZ

To test the effect of inactivation of the fimZ gene on L-glutamate production, DNA fragments from the chromosome of the above-described E. coli strain MG1655 Δ-fimZ::cat can be transferred to the E. coli L-glutamate-producing strain VL334thrC$^+$ (EP 1172433) by P1 transduction (Miller, J. H. Experiments in Molecular Genetics, Cold Spring Harbor Lab. Press, 1972, Plainview, N.Y.) to obtain the strain VL334thrC$^+$-ΔfimZ. Both strains, VL334thrC$^+$ and VL334thrC$^+$-ΔfimZ, can be grown for 18-24 hours at 37° C. on L-agar plates. Then, one loop of the cells can be transferred into test tubes containing 2 ml of fermentation medium. The fermentation medium contains glucose (60g/l), ammonium sulfate (25 g/l), $KH_2PO_4$ (2g/l), $MgSO_4$ (1 g/l), thiamine (0.1 mg/ml), L-isoleucine (70 μg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 20

Production of L-phenylalanine by E. coli AJ12739-ΔfimZ

To test the effect of inactivation of the fimZ gene on L-phenylalanine production, DNA fragments from the chromosome of the above-described E. coli MG1655 ΔfimZ::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain strain AJ12739-ΔfimZ.

Both strains, AJ12739-ΔfimZ and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 21

Production of L-tryptophan by E. coli SV164 (pGH5)-ΔfimZ

To test the effect of inactivation of the fimZ gene on L-tryptophan production, DNA fragments from the chromosome of the above-described E. coli strain MG1655 ΔfimZ::cat can be transferred to the tryptophan-producing E. coli strain SV164 (pGH5) by P1 transduction (Miller, J. H. Experiments in Molecular Genetics, Cold Spring Harbor Lab. Press, 1972, Plainview, N.Y.) to obtain the strain SV164(pGH5)-ΔfimZ.

Both strains, SV164(pGH5)-ΔfimZ and SV164(pGH5), can be cultivated with shaking at 37° C. for 18 hours in 3 ml of nutrient broth supplemented with tetracycline (20 mg/l, marker of pGH5 plasmid). The obtained cultures (0.3 ml each) can be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 2, but should be sterilized in separate groups (A, B, C, D, E, F, and H), as shown, to avoid adverse interactions during sterilization.

Example 22

Production of L-proline by E. coli 702ilvA-ΔfimZ

To test the effect of inactivation of the fimZ gene on L-proline production, DNA fragments from the chromosome of the above-described E. coli strain MG1655 ΔfimZ::cat can be transferred to the proline-producing E. coli strain 702ilvA by P1 transduction (Miller, J. H. Experiments in Molecular Genetics, Cold Spring Harbor Lab. Press, 1972, Plainview, N.Y.) to obtain the strain 702ilvA-ΔfimZ. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains 702ilvA and 702ilvA-ΔfimZ, can be grown for 18-24 hours at 37° C. on L-agar plates. Then, these strains can be cultivated under the same conditions as in Example 8.

Example 23

Production of L-arginine by E. coli 382-ΔfimZ

To test the effect of inactivation of the fimZ gene on L-arginine production, DNA fragments from the chromosome of the above-described E. coli strain MG1655 ΔfimZ::cat can be transferred to the arginine-producing E. coli strain 382 by P1 transduction (Miller, J. H. Experiments in Molecular Genetics, Cold Spring Harbor Lab. Press, 1972, Plainview, N.Y.) to obtain strain 382-ΔfimZ.

Both strains, 382-ΔfimZ and 382, can be cultivated with shaking at 37° C. for 18 hours in 3 ml of nutrient broth, and 0.3 ml of the obtained cultures can be inoculated into 3 ml of a fermentation medium in 20×200-mm test tubes and cultivated at 32° C. for 48 hours on a rotary shaker.

After the cultivation, the amount of L-arginine which accumulates in the medium can be determined by paper chromatography using the following mobile phase:butanol:acetic acid:water=4:1:1 (v/v). A solution of ninhydrin (2%) in acetone can be used as a visualizing reagent. A spot containing L-arginine can be cut out, L-arginine can be eluted with 0.5% water solution of $CdCl_2$, and the amount of L-arginine can be estimated spectrophotometrically at 540 nm.

The composition of the fermentation medium (g/l) is as follows:

| | |
|---|---|
| Glucose | 48.0 |
| $(NH_4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180 ° C. for 2 hours. The pH is adjusted to 7.0.

Example 24

Elimination of the Cm Resistance Gene (Cat Gene) from the Chromosome of L-Amino Acid-Producing E. coli Strains The Cm resistance gene (cat gene) can be eliminated from the chromosome of the L-amino acid-producing strain using the int-xis system. For that purpose, an L-amino acid-producing strain having DNA fragments from the chromosome of the above-described E. coli strain MG1655 ΔsfmACDHF-fimZ::cat or MG1655 ΔfimZ::cat transferred by P1 transduction (see Examples 3-23), can be transformed with plasmid pMWts-Int/Xis. Transformant clones can be selected on the LB-medium containing 100 μg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of $Cm^S AP^R$ variants. Elimination of the cat gene from the chromosome of the strain can be verified by PCR. Locus-specific primers P23 (SEQ ID NO:39) and P24 (SEQ ID NO:40) can be used in PCR for the verification. Conditions for PCR verification can be as described above. The PCR product obtained in reaction with cells having the eliminated cat gene as a template, should be ~0.1 kbp in length. Thus, the L-amino acid-producing strain with the inactivated sfmACDHF-fimZ cluster or fimZ gene and eliminated cat gene can be obtained.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acid of a bacterium of the Enterobacteriaceae family can be enhanced.

The invention claimed is:

1. A method for producing an L-amino acid comprising:
   cultivating an L-amino acid-producing bacterium of the Enterobacteriaceae family in a medium to produce and excrete said L-amino acid into the medium, and collecting said L-amino acid from the medium,
   wherein said bacterium has been modified to attenuate expression of genes of sfmACDFH-fimZ gene cluster or fimZ gene.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

5. The method according to claim 1, wherein said expression is attenuated by inactivation of the gene.

6. The method according to claim 1, wherein said bacterium belongs to the genus *Escherichia*.

7. The method according to claim 1, wherein said bacterium belongs to genus *Pantoea*.

* * * * *